(12) United States Patent
Cheng et al.

(10) Patent No.: US 11,466,055 B2
(45) Date of Patent: Oct. 11, 2022

(54) VIRUS-LIKE NANOPARTICLES FOR ORAL DELIVERY

(71) Applicant: The Regents of the University of California, Oakland, CA (US)

(72) Inventors: R. Holland Cheng, Oakland, CA (US); Chun Chieh Chen, Oakland, CA (US); Mohammad Ali Baikoghli, Oakland, CA (US); Marie Stark, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 21 days.

(21) Appl. No.: 15/734,877

(22) PCT Filed: Jun. 6, 2019

(86) PCT No.: PCT/US2019/035823
§ 371 (c)(1),
(2) Date: Dec. 3, 2020

(87) PCT Pub. No.: WO2019/236870
PCT Pub. Date: Dec. 12, 2019

(65) Prior Publication Data
US 2021/0221850 A1    Jul. 22, 2021

Related U.S. Application Data

(60) Provisional application No. 62/681,637, filed on Jun. 6, 2018.

(51) Int. Cl.
| | | |
|---|---|---|
| *A61K 39/00* | (2006.01) | |
| *C07K 14/005* | (2006.01) | |
| *A61K 38/00* | (2006.01) | |
| *C07K 14/195* | (2006.01) | |
| *C07K 14/02* | (2006.01) | |
| *C07K 14/62* | (2006.01) | |
| *C12N 7/00* | (2006.01) | |

(52) U.S. Cl.
CPC ............ *C07K 14/005* (2013.01); *C07K 14/62* (2013.01); *C12N 7/00* (2013.01); *A61K 38/00* (2013.01); *C12N 2770/28122* (2013.01); *C12N 2770/28123* (2013.01)

(58) Field of Classification Search
CPC ...... C07K 14/005; A61K 38/00; A61K 39/00; A61P 31/12; A61P 31/14
See application file for complete search history.

(56) References Cited

U.S. PATENT DOCUMENTS

| | | |
|---|---|---|
| 8,906,862 B2 | 12/2014 | Cheng et al. |
| 8,906,863 B2 | 12/2014 | Cheng et al. |
| 2013/0216588 A1 | 8/2013 | Chou et al. |
| 2017/0107261 A1* | 4/2017 | Cheng .................. A61K 9/5169 |

FOREIGN PATENT DOCUMENTS

| | | | |
|---|---|---|---|
| WO | 2010/074542 A2 | | 1/2010 |
| WO | WO2010074542 | * | 7/2010 |
| WO | 2019/178288 A2 | | 9/2019 |

OTHER PUBLICATIONS

International Search Report in PCT/US2019/035823, dated Nov. 20, 2019.
Supplemental European Search Report in EP 19 81 5509, dated Feb. 22, 2022, 16 pages.
Chen CC, et al. Surface functionalization of hepatitis E virus nanoparticles using chemical conjugation methods. JoVE (Journal of Visualized Experiments). May 11, 2018(135):e57020.
Stark, et al. "Structural characterization of site-modified nanocapsid with monodispersed gold clusters." Scientific reports 7, No. 1 (2017): 1-11.
Stark, Marie. "Recombinant nanocapsid for targeted theranostic delivery." Jyväskylä studies in biological and environmental science 334 (2017).

* cited by examiner

*Primary Examiner* — Barry A Chestnut
(74) *Attorney, Agent, or Firm* — Kilpatrick Townsend & Stockton LLP

(57) ABSTRACT

A Hepatitis E virus (HEV)-based virus like nanoparticle (HEVNP) made with a modified capsid protein containing at least a portion of open reading frame 2 (ORF2) protein conjugated with gold nanocluster is provided. Also provided are methods of targeted delivery of a nucleic acid using the HEVNP.

19 Claims, 26 Drawing Sheets
Specification includes a Sequence Listing.

Figure 1C:
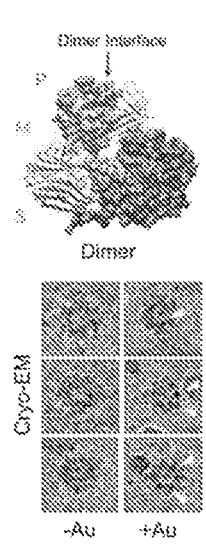

Figure 1A                    Figure 1B

Figure 3A
Figure 3B
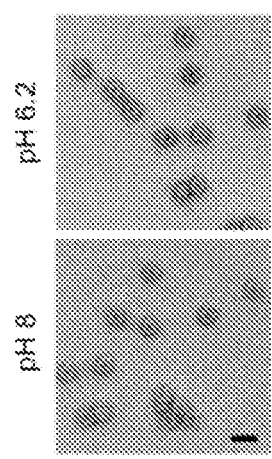
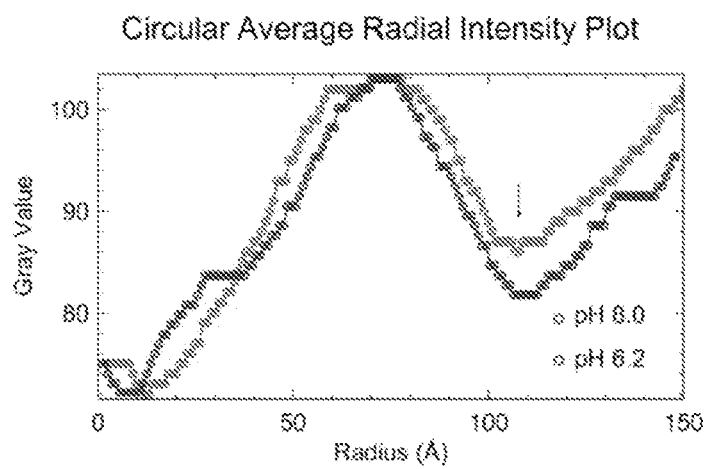
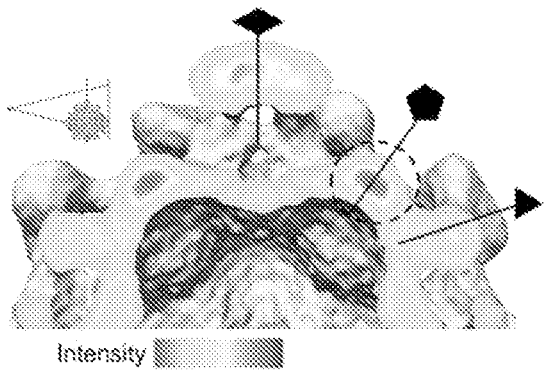
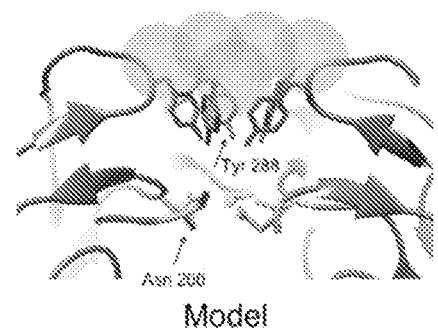
Figure 3C
Figure 3D

Figure 8

Enhanced HEVNP stability via gold-nanocluster conjugation to resist high pH degradation.

Figure 9

HEVNP DECAMER

Dual-Domain Insertion

Figure 24

HEVNP + bp-tag + bp-anchor + Protein of Interest

Genetic and/or Chemical Insertion of bp-tag on P or the M Domain of HEVNP

HEVNP Dimer bp-tag

Attached Protein of Interest bp-anchor

Figure 25

Sequence alignment for all 6 versions of ORF2 (SEQ ID NO:1-6):

```
HEV_ORF2_Genotype_1        ---------------mrprpillllmflpmlpapppgqpsqrrrgrrsggsgggfwgdra 46
HEV_ORF2_Genotype_2        ---------------mrprplllfllflpmlpapptgqpsqrrrgrrsggtgggfwgdrv 46
HEV_ORF2_Genotype_6        ---------------mrpravillflmllpmlpappagqpsqrrrgrrsggsgggfwgdrv 46
HEV_ORF2_Genotype_5        mnnmflcfacgyatmrpraillllvvllpmlpappagqssqrrrgrrsggagsgfwgdrv 60
HEV_ORF2_Genotype_3        ---------------mrpravlllffvllpmlpappagqpsqrrrgrrsggagggfwgdrv 46
HEV_ORF2_Genotype_4        ---------------mrpravlllffvllpmlpappagqpsqrrrgrrsgqtgggfwgdrv 46
                                          ****  ***  : **********  ** **********  *  ******.

HEV_ORF2_Genotype_1        dsqpfaipyihptnpfapdvtaaagagprvrqparplgsawrdqaqrpaaasrrrpttag 106
HEV_ORF2_Genotype_2        dsqpfaipyihptnpfapdvaaasgsgprlrqparplgstwrdqaqrpsaasrrrpatag 106
HEV_ORF2_Genotype_6        dsqpfalpyihptnpfasdvstsagagararqasrplgsawrdqsqrpsaasarrrptpag 106
HEV_ORF2_Genotype_5        dsqpfalpyihptnpfasdtiaatgtgarsrqsarplgsawrdqtqrppaasrrrstptg 120
HEV_ORF2_Genotype_3        dsqpfalpyihptnpfaadvvsqsgagarprqpprplgsawrdqsqrpsaaprrrsapag 106
HEV_ORF2_Genotype_4        dsqpfalpyihptnpfasdiptatgagarprqparplgsawrdqsqrpaaparrrsapag 106
                           ******:*********** *   :*:*  *  ** *****:****:***  *  *** : :*

HEV_ORF2_Genotype_1        aapltavapahdtppvpdvdsrgailrrqynlstspltssvatgtnlvlyaaplsplipl 166
HEV_ORF2_Genotype_2        aaaltavapahdtspvpdvdsrgailrrqynlstspltssvasgtnlvlyaaplnpplpl 166
HEV_ORF2_Genotype_6        aspltavapapdttpvpdvdsrgailrrqynlstspltstvasgtnlvlyaaplgpllpl 166
HEV_ORF2_Genotype_5        aspltavapapdtrpvpdvdsrgailrrqynlstspltstiasgtnlvlyaaplspllpl 180
HEV_ORF2_Genotype_3        aapltaispapdtapvpdvdsrgailrrqynlstspltssvasgtnlvlyaaplnpllpl 166
HEV_ORF2_Genotype_4        aspltavapapdtapvpdvdsrgailrrqynlstspltstiatgtnlvlyaaplspllpl 166
                           *: ***::** **  ********************** ::*:*:******.* ***

HEV_ORF2_Genotype_1        qdgtnthimateasnyaqyrvvratiryrplvpnavggyaisisfwpqttttptsvdmns 226
HEV_ORF2_Genotype_2        qdgtnthimateasnyaqyrvaratiryrplvpnavggyaisisfwpqttttptsvdmns 226
HEV_ORF2_Genotype_6        qdgtnthimateasnyaqyrviratiryrplvpnavggyaisisfwpqttttptsvdmns 226
HEV_ORF2_Genotype_5        qdgtnthimateasnyaqyrvvratiryrplvpnavggyaisisfwpqttttptsvdmns 240
HEV_ORF2_Genotype_3        qdgtnthimateasnyaqyrvvratiryrplvpnavggyaisisfwpqttttptsvdmns 226
HEV_ORF2_Genotype_4        qdgtnthiiateasnyaqyrvvratiryrplvpnavggyaisisfwpqttttptsvdmns 226
                           ********:*********** ***************************************

HEV_ORF2_Genotype_1        itstdvrilvqpgiasehvipserlhyrnqgwrsvetsgvaeeeatsglvmlcihgslvn 286
HEV_ORF2_Genotype_2        itstdvrilvqpgiaselvipserlhyrnqgwrsvetsgvaeeeatsglvmlcihgspvn 286
HEV_ORF2_Genotype_6        itstdvrilvqpglaseliipserlhyrnqgwrsvetsgvaeeeatsglvmlcihgspvn 286
HEV_ORF2_Genotype_5        itstdvrivvqpgiaselvipserlhyrnqgwrsvetsgvaeeeatsglvmlcihgspvn 300
HEV_ORF2_Genotype_3        itstdvrilvqpgiaselvipserlhyrnqgwrsvettgvaeeeatsglvmlcihgspvn 286
HEV_ORF2_Genotype_4        itstdvrilvqpgiaselvipserlhyrnqgwrsvetsgvaeeeatsglvmlcihgspvn 286
                           ********:****:***  :******************:*****************  **

HEV_ORF2_Genotype_1        sytntpytgalglldfalelefrnltpgntntrvsryssstarhrlrrgadgtaelttaa 346
HEV_ORF2_Genotype_2        sytntpytgalglldfalelefrnlttcntntrvsrysstarhs-argadgtaelttaa 345
HEV_ORF2_Genotype_6        sytntpytgalglldfalelefrnltpgntntrvsrytstarhrlrrgpdgtaelttaa 346
HEV_ORF2_Genotype_5        sytntpytgalglldfalelefrnltpgntntrvsryssstarhrlhrgadgtaelttaa 360
HEV_ORF2_Genotype_3        sytntpytgalglldfalelefrnltpgntntrvsrytstarhrlrrgadgtaelttaa 346
HEV_ORF2_Genotype_4        sytntpytgalglldfalelefrnltpgntntrvsrysssarhklcrgpdgtaelttaa 346
                           *************************  ********:*:***   ** ***********

HEV_ORF2_Genotype_1        trfmkdlyftstngvgeigrgialtlfnladtllgglptelissaggqlfysrpvvsang 406
HEV_ORF2_Genotype_2        trfmkdlhftqlngvgevgrgialtllnladtllgglptelissaggqlfysrpvvsang 405
HEV_ORF2_Genotype_6        trfmkdlyftgsnglgevgrgialtlfnladtllgglptelissaggqlfysrpvvsang 406
HEV_ORF2_Genotype_5        trfmkdlxftgsngigevgrgialtlfnladtllgglptelissaggqlfysrpvvsang 420
HEV_ORF2_Genotype_3        trfmkdlhftgtngvgevgrgialtlfnladtllgglptelissaggqlfysrpvvsang 406
HEV_ORF2_Genotype_4        trfmkdlhftgtngvgevgrgialtllnladtllgglptelissaggqlfysrpvvsang 406
                           ******  **.  **:**:************:***************************

HEV_ORF2_Genotype_1        eptvklytsvenaqqdkgiaiphdidlgesrvviqdydnqheqdrptpspapsrpfsvlr 466
HEV_ORF2_Genotype_2        eptvklytsvenaqqdkgvaiphdidlgdsrvviqdydnqheqdrptpspapsrpfsvlr 465
HEV_ORF2_Genotype_6        eptvklytsvenaqqdkgiaipheidlgdsrvviqdydnqheqdrptpspapsrpfsvlr 466
HEV_ORF2_Genotype_5        eptvklytsvenaqqdkgiaiphdidlgdsrvviqdydnqheqdrptpspapsrpfsvlr 480
HEV_ORF2_Genotype_3        eptvklytsvenaqqdkgitiphdidlgdsrvviqdydnqheqdrptpspapsrpfsvlr 466
HEV_ORF2_Genotype_4        eptvklytsvenaqqdkgiaiphdidlgesrvviqdydnqheqdrptpspapsrpfsvlr 466
                           *****************::***:*:***.***********************************

HEV_ORF2_Genotype_1        andvlwlsltaaeydqstygsstgpvyvsdsvtlvnvatgaqavarsldwtkvtldgrpl 526
HEV_ORF2_Genotype_2        andvlwlsltaaeydqstygsstgpvyisdsvtlvnvatgaqavarsldwskvtldgrpl 525
HEV_ORF2_Genotype_6        vndvlwitltaaeydqttygsttnpmyvsdtvtfvnvatgaqgvaraldwskvtfdgrpl 526
HEV_ORF2_Genotype_5        vndvlwltmtaaeydqttygtstdpvyvsdtvtfvnvatgaqgvarsldwskvtldgrpl 540
HEV_ORF2_Genotype_3        andvlwlsltaaeydqttygsstnpmyvsdtvtfvnvatgaqavarsldwskvtldgrpl 526
HEV_ORF2_Genotype_4        andvlwlsltaaeydqttygsstnpmyvsdtvtfvnvatgtqgvsrsldwskvtldgrpl 526
                           .*****::*********:****:***:*.*:*:**:*****:*.*.*:****:**:*****
```

Figure 25 (Cont.)

```
HEV_ORF2_Genotype_1    sttqqysktffvlplrgklsfweagttkagypynynttasdqllvenaaghrvaistytt  586
HEV_ORF2_Genotype_2    ptveqysktffvlplrgklsfweagttkagypynynttasdqilienaaghrvaistytt  585
HEV_ORF2_Genotype_6    ttvqqygksffvlplrgklsfweagtvkagypynynttasdqilvenapghrvcistytt  586
HEV_ORF2_Genotype_5    ttiqrhsknyfvlplrgklsfweagttkagypynynttasdqilienaaghrvcistytt  600
HEV_ORF2_Genotype_3    ttiqqysktfyvlplrgklsfweagttkagypynynttasdqilienaaghrvaistytt  586
HEV_ORF2_Genotype_4    ttiqqysktffvlplrgklsfweagttkagypynynttasdqilienapghrvcistytt  586
                       *  ::: *.::***************.***************:*:*** ****.******

HEV_ORF2_Genotype_1    slgagpvsisavavvlaphsalalledtmdyparahtfddfcpecrplglqgcafqstvae  646
HEV_ORF2_Genotype_2    rlgagpvaisaaavlaprsalalledtfdypgrahtfddfcpecralglqgcafqstvae  645
HEV_ORF2_Genotype_6    nlgsgpvsisavgvlaphaataaledtadsparahtfddfcpecrilglqgcayqstaae  646
HEV_ORF2_Genotype_5    slgsgpvsvsgvgvlaphaalavledtvdyparahtfddfcpecrtlglqgcafqstvae  660
HEV_ORF2_Genotype_3    slgagptsisavgvlaphsalavledttdyparahtfddfcpecrtlglqgcafqstiae  646
HEV_ORF2_Genotype_4    nlgsgpvsisavgvlaphsalaaledtvdyparahtfddfcpecralglqgcafqstvae  646
                       **:**.::*...****::*  * **** * *.************ ******:*** **

HEV_ORF2_Genotype_1    lqrlkmkvgktrel    660
HEV_ORF2_Genotype_2    lqrlkvkvgktrel    659
HEV_ORF2_Genotype_6    lqrlkmkvgksref    660
HEV_ORF2_Genotype_5    lqrlkmrvgktref    674
HEV_ORF2_Genotype_3    lqrlkmkvgktres    660
HEV_ORF2_Genotype_4    lqrlkmkvgktqey    669
                       *****::***::*
```

VIRUS-LIKE NANOPARTICLES FOR ORAL DELIVERY

RELATED APPLICATION

This application claims priority to U.S. Provisional Patent Application No. 62/681,637, filed Jun. 6, 2018, the contents of which are hereby incorporated by reference in the entirety for all purposes.

STATEMENT OF US GOVERNMENT RIGHTS TO THIS APPLICATION

The underlying invention of this application was made with U.S. Government support under Grant Nos. EB021230, CA198889, and CA-D*MCB-7399-H, awarded by the National Institutes of Health and the National Institute of Food and Agriculture. The Government has certain rights in this invention.

REFERENCE TO SUBMISSION OF A SEQUENCE LISTING AS A TEXT FILE

The Sequence Listing written in file 081906-1220169_SL.txt created on Dec. 2, 2020, 61,440 bytes, machine format IBM-PC, MS-Windows operating system, is hereby incorporated by reference in its entirety for all purposes.

BACKGROUND OF THE INVENTION

Virus-like particles (VLPs) can serve as nanocarriers for targeted delivery of diagnostics and therapeutics regimes, such as DNA/RNA and a variety of chemotherapeutics. Hepatitis E virus (HEV) is an enteric-transmitted virus that causes acute liver inflammation in humans. HEV virus-like particles (HEV VLPs) are capsid protein icosahedral cages that can be produced by expression of the major capsid protein HEV Open Reading Frame 2 (ORF2) in a eukaryotic expression system. HEV VLPs are stable in acid and proteolytic environments, a feature that is required for the natural transmission route of HEV. Thus, HEV VLPs represent a promising nano-carrier that can be exploited, e.g., for the delivery of therapeutic agents, imaging agents, or vaccines.

Taking advantage of HEV's natural infection via feco-oral routes, REV-based delivery technology is designed for therapeutic use by means of oral administration. Although HEV VLP is reasonably stable, exposure to the extreme pH and enzymatic activities in the digestive tract still can present certain challenges. As such, there exists a pressing need for developing novel modifications of HEV VLP to achieve improved stability under these conditions and therefore generate a more reliable HEV-based delivery system. The present invention fulfills this and other related needs.

BRIEF SUMMARY OF THE INVENTION

The present invention provides a new and improved HEV nanoparticle (HEVNP) that has surface-conjugated gold nanocluster with improved stability, especially under higher pH values, and are therefore particularly suitable for delivery of an therapeutic modality carried by the HEV-VLP via oral administration.

In a first aspect, the present invention provides a modified capsid protein comprising a portion of hepatitis E virus (HEV) open Reading Frame 2 (ORF2) protein, with at least one amino acid in the 342-344, 402-408, 510-514, 493-498, 570-579, 529-536, or 520-525 segment of the HEV ORF2 protein amino acid sequence set forth in SEQ ID NO:1 or the corresponding segment of SEQ ID NO:2, 3, 4, 5, or 6 replaced with a cysteine, and the cysteine is in turn conjugated with a nanocluster of an element selected from Group 3 through 18 having an atomic number greater than 20.

In some embodiments, the element is gold or silver. In some embodiments, amino acid residue 342 or 573 (or both 342 and 573) of the HEV ORF2 protein amino acid sequence set forth in SEQ ID NO:1 or the corresponding residue of SEQ ID NO:2, 3, 4, 5, or 6 is replaced with a cysteine. In some embodiments, the cysteine is chemically derivatized, for example, with a 6-carbon spacer pMBA44, and conjugated with the gold nanocluster via a linker, for example, a maleimide linker. In some embodiments, the nanocluster is about 2-3 nm horizontally and about 2 nm vertically from the cysteine. In some embodiments, the nanocluster is about 1.5-3 nm in diameter.

In a second aspect, the present invention provides a composition comprising (1) the modified HEV ORF2 capsid protein described above and herein and (2) a bioactive agent (e.g., a heterologous polynucleotide, DNA or RNA, or a heterologous polypeptide, such as insulin protein or an insulin-encoding DNA or RNA) encapsulated in an HEV virus-like particle (VLP) formed by the modified capsid protein.

In some embodiments, the composition further comprises a pharmaceutically acceptable excipient, for example, one or more excipients particularly suitable for a formulation intended for oral administration.

In a third aspect, the present invention provides a method for targeted delivery of a bioactive agent (e.g., a heterologous polynucleotide, DNA or RNA, or a heterologous polypeptide, such as insulin protein or an insulin-encoding DNA or RNA) to liver cells. The method includes a step of contacting a liver cell with any of the compositions described above and herein.

In some embodiments, the liver cell is within a patient's body, and the contacting step comprises administration of the composition described above and herein to the patient. In some embodiments, the administration is oral administration. In some embodiments, the modified capsid protein is derivatized with pMBA44 and conjugated to a gold nanocluster via maleimide linker. In some embodiments, the bioactive agent is a polynucleotide sequence encoding an insulin, proinsulin, or pre-proinsulin. In other embodiments, the bioactive agent is an insulin polypeptide. In some embodiments, the patient has been diagnosed with a disease or condition treatable by the bioactive agent, e.g., diabetes.

BRIEF DESCRIPTION OF THE DRAWINGS

FIGS. 1A-1E: Surface functionalization of HEV-VLP with AuNC. (FIG. 1A) Capsid protein composition of HEVNP includes dimeric subunits comprised of shell (s), middle (m), and protrusion (p) domains. P-domain is stabilized with a proline-rich hinge connected to the M-domain, while the S domain stabilized the icosahedral shell. The P-domain is utilized for surface functionalization. Here, the residue 573 (highlighted in yellow) was replaced with a Cysteine to allow for thiol-exchange disulfide bonding. The dimers form pentamers (thus decamers), stabilized by local intermolecular interactions at the 5-fold axis, and assemble into capsid shell of HEVNP via Ca+ bridges at the 3-fold. (FIG. 1B) Au102-pMBA-C6-Maleimide (AuNC) is conjugated to the 573C through thiol-exchange reaction. (FIG.

1C) Cryo-Electron Microscopy was employed to characterize the AuNC and to process data for 3D reconstruction through single particle analysis. Comparison between Au-free and Au-conjugated is characterized by high intensity regions pointed by the arrows. (FIG. 1D) Resulting 3D reconstructions with HEVNP as control and HEVNP+Au102C6, show high intensity regions around 5-fold axis (FIG. 1E), suggesting AuNC localization and stabilization around the 5-fold axis.

Figure 2A:
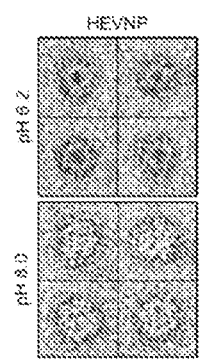
Figure 2B:
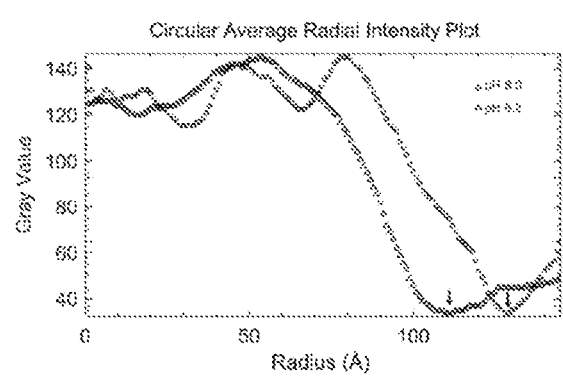
Figure 2C:

FIGS. 2A-2C: Stability of HEVNP is reduced at high pH as a result of weakened intermolecular interactions at 5-fold interface. (FIG. 2A) TEM images of HEVNP at pH 6.2 and pH 8.0; showing larger particles at pH 8.0. (FIG. 2B) circular averaging and 1-D intensity profiling. It was observed that the HEVNP at pH 8.0 were about 10-15% larger than HEVNP without AuNC. (FIG. 2C) Molecular modeling was carried out and it was observed that intermolecular interactions were reduced at the 5-fold as pH is increased to 8.

FIGS. 3A-3D: Enhanced stability of HEVNP after AuNC-C6 conjugation. (FIG. 3A) TEM images of HEVNP conjugated to AuNC-C6 revealed that the overall size of the HEVNP does not change with increased pH. (FIG. 3B) circular averaging and 1-D intensity profiling. The data shows no changes to the HEVNP size as a result of increased pH. (FIG. 3C) 2D intensity slice cross-section analysis reveals high intensity regions at the 5-fold of the cryo-EM reconstructed 3D density map. (FIG. 3D) A model showing the mechanism by which critical intermolecular interactions are potentially preserved by colocalization of AuNC-C6 around the icosahedral 5-fold axis of HEVNP.

Figure 4:
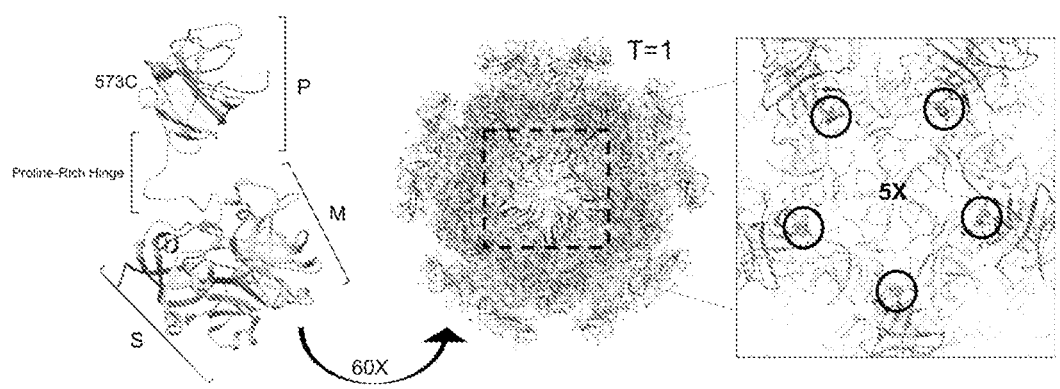

FIG. 4: HEVNP monomer showing the 3 distinct domains of HEVNP. The shell domain (S) (AA: 118-317) is critical in inter-subunit interactions, stabilizing the icosahedral capsid. The middle domain (M) (AA: 318-451) binds and interacts with the S domain. The protrusion domain (P) (452-606) forms a dimeric spike at the 2-fold axis. The M domain is connected to the P domain via a proline-rich hinge, which facilitates the topological changes in the protruding spikes.

Figure 5:
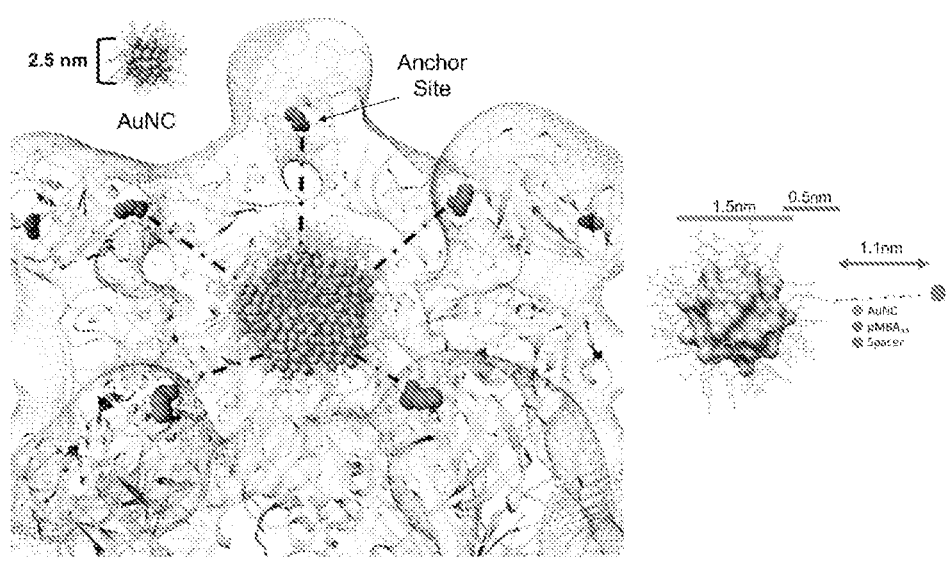

FIG. 5: Modeling of AuNC conjugation to HEVNP at position #N573C via extendable spacer arm. Co-localization of AuNC around the 5-fold icosahedral axis of HEVNP.

Figure 6:
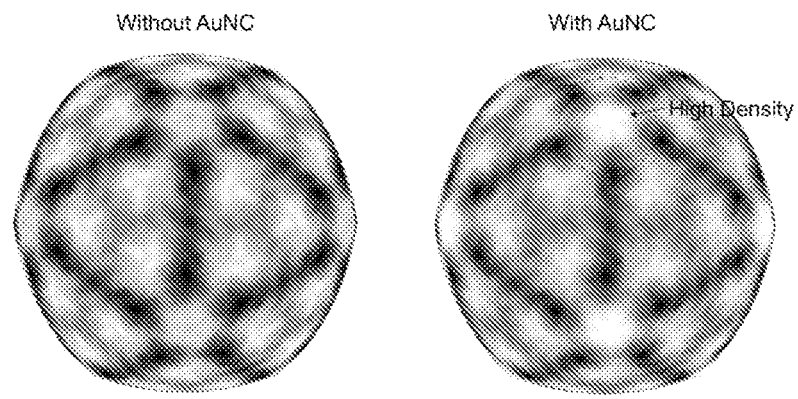

FIG. 6: Radial cueing at the S domain 5-fold showing the high density regions observed in the AuNC conjugated and the absence of these high density regions in the WT construct.

Figure 7:
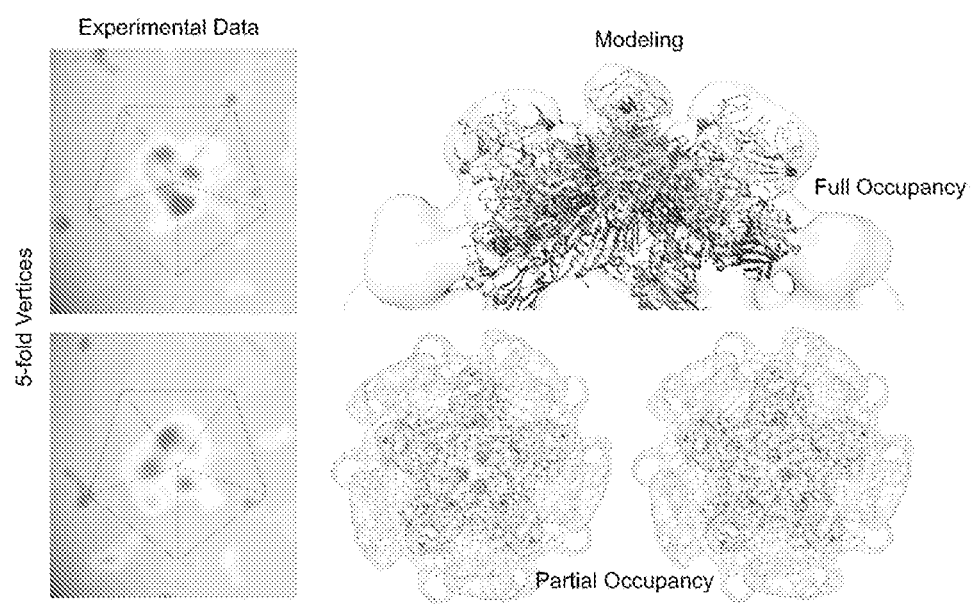

FIG. 7: Comparison of experimental data and modeling data showing the electron dense regions around the 5-fold axis. Full occupancy with allow 5 unique densities around the 5-fold, where are partial occupancy would allow 4 or less AuNC to co-localize around the 5-fold. Cryo-EM Single Patrice Reconstruction analysis indicates that the AuNC are horizontally (normal to 5-fold axis) flexible in the range of 2-3 nm and about 2 nm vertically.

FIG. 8: Modeling of AuNC co-localization around the 5-fold to preserve critical intermolecular interactions between TYR288 and ASN200. In B, the flexibility of the P dimers allow for bending towards the 5-fold center; this structural geometry is not observed in the HEVNP control map without AuNC conjugation. And in C, summary of P domain flexibility and the preservation of TYR288 and ANS200.

Figure 9:
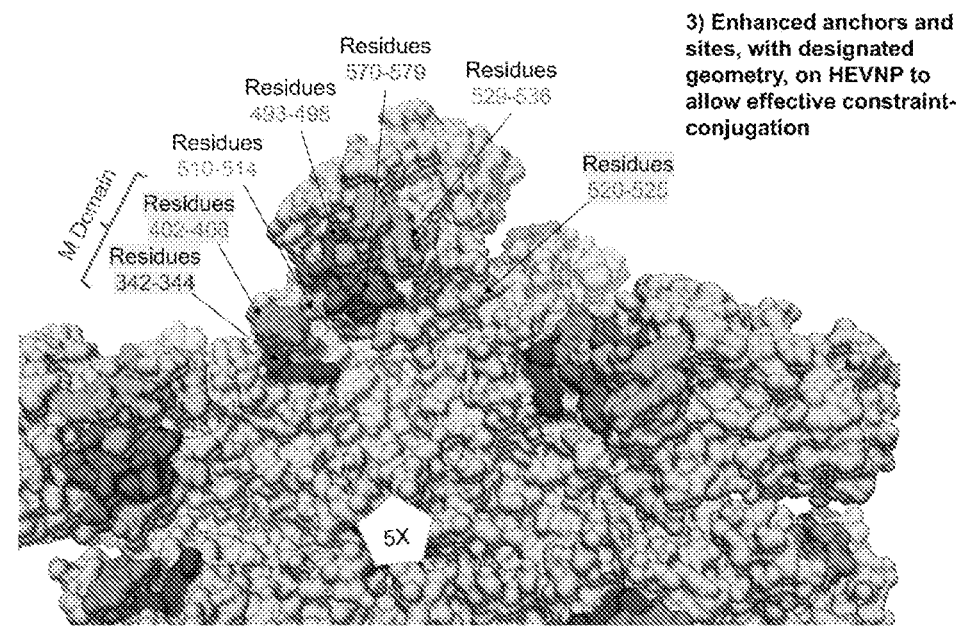

FIG. 9: Additional anchor sites within residues 402-408, 342-344, and on protrusion domain, residues: 521-526, for enhanced anchors and site, with designated geometry, on HEVNP to allow effective constraint-conjugation towards stabilization of HEVNP.

Figure 10:
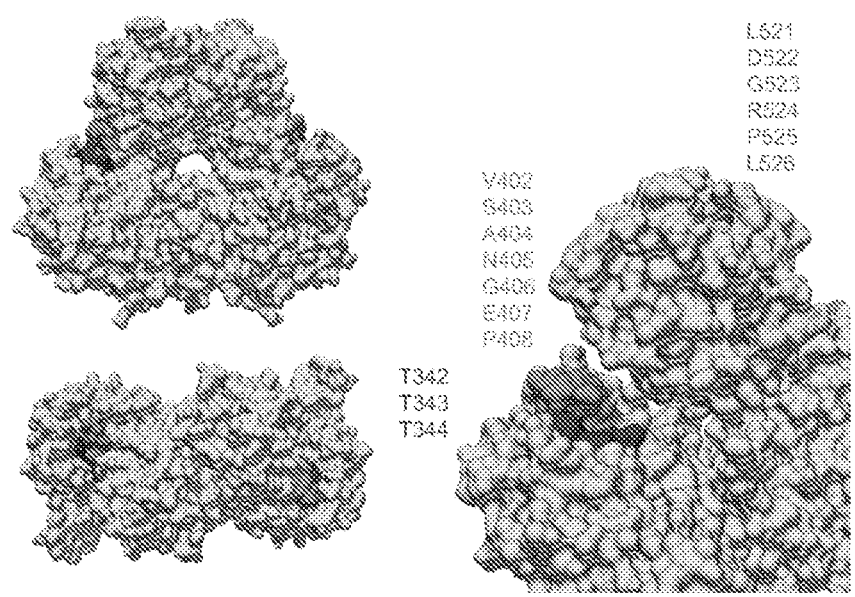

FIG. 10: New compositional modifications for cysteine replacement on residues 402-408, 342-344, and on protrusion domain, residues: 521-526.

Figure 11:
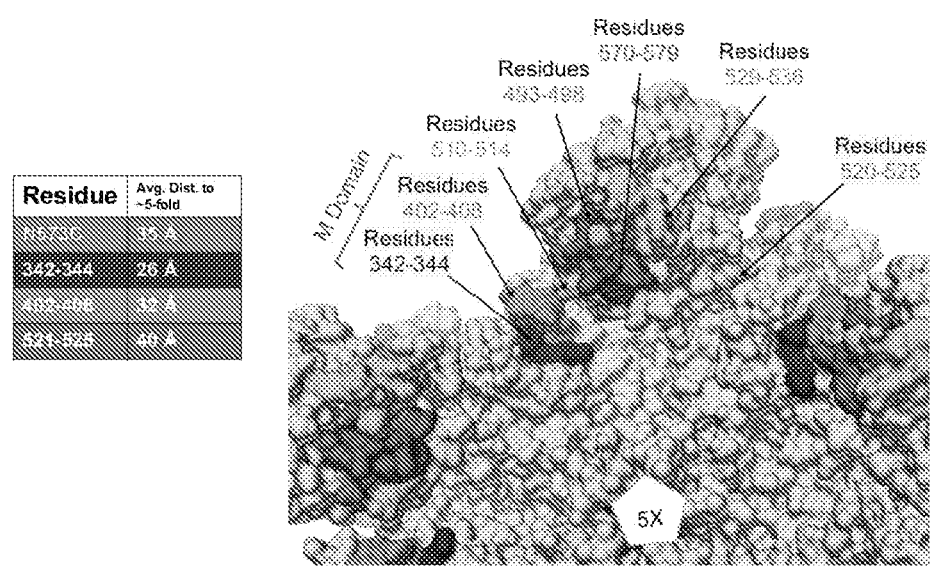

FIG. 11: Relative average distance to the 5-fold axis, compared to our previously established engineered N573C site.

Figure 12:
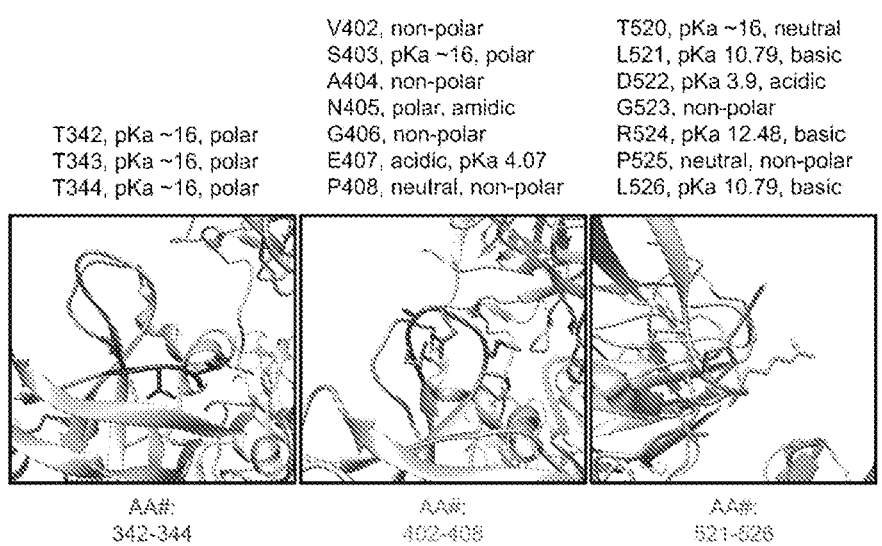

FIG. 12: Composition of amino acid on selected loops. First two from left are from M domain and last one (yellow) is from the P domain of HEVNP.

Figure 13:
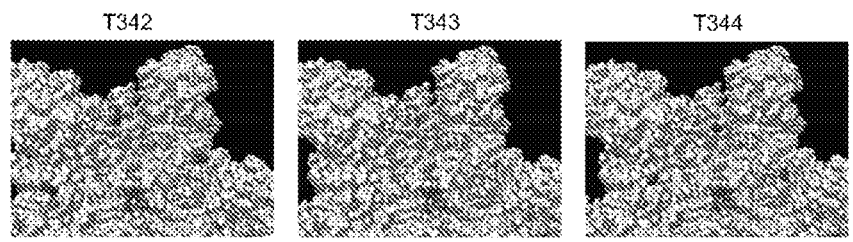

FIG. 13: Position of selected amino acids (324-344) relative to the 5-fold axis (marked with magenta).

Figure 14:
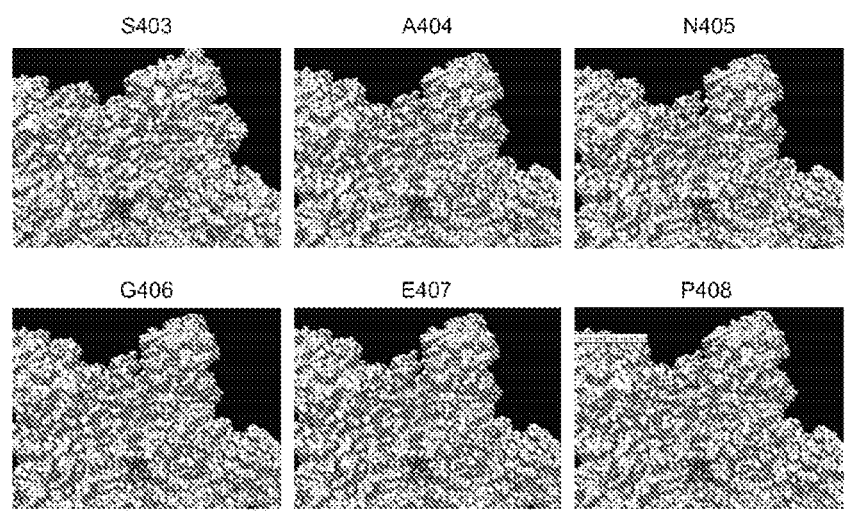

FIG. 14: Position of selected amino acids (402-408) relative to the 5-fold axis (marked with magenta).

Figure 15:
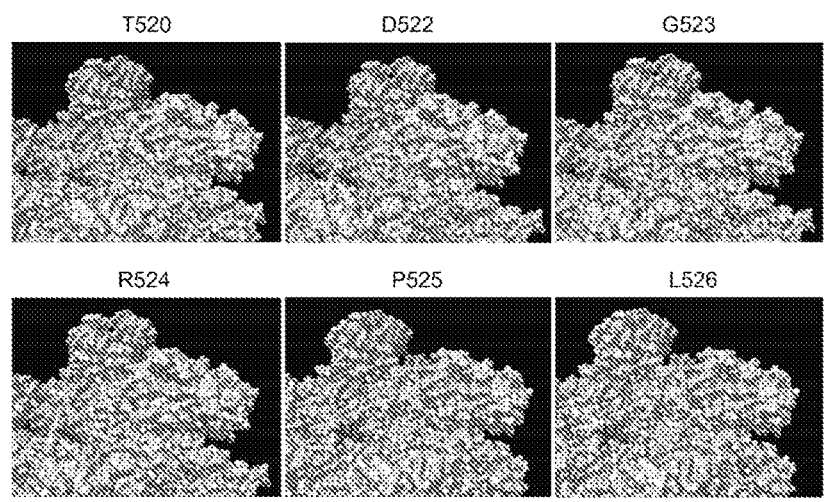

FIG. 15: Position of selected amino acids (521-526) relative to the 5-fold axis (marked with magenta).

Figure 16:
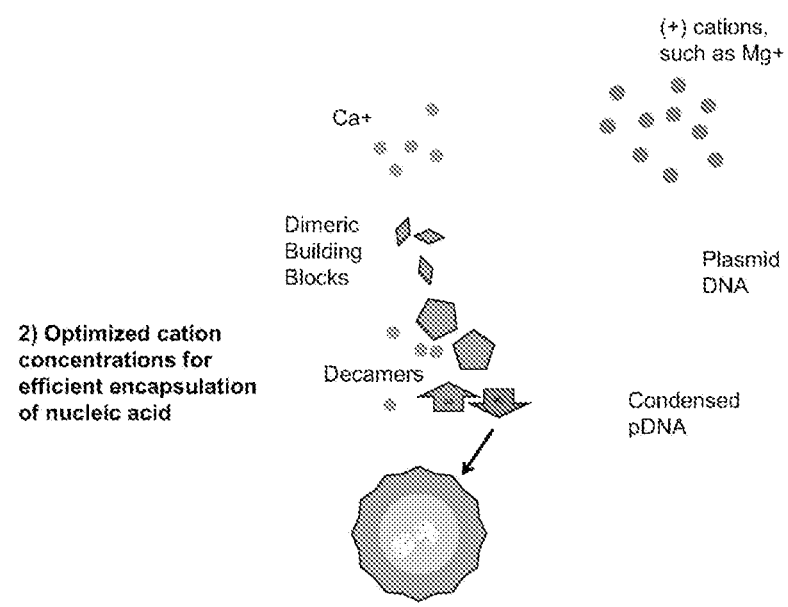

FIG. 16: Optimized cation concentrations for efficient encapsulation of nucleic acid.

Figure 17:
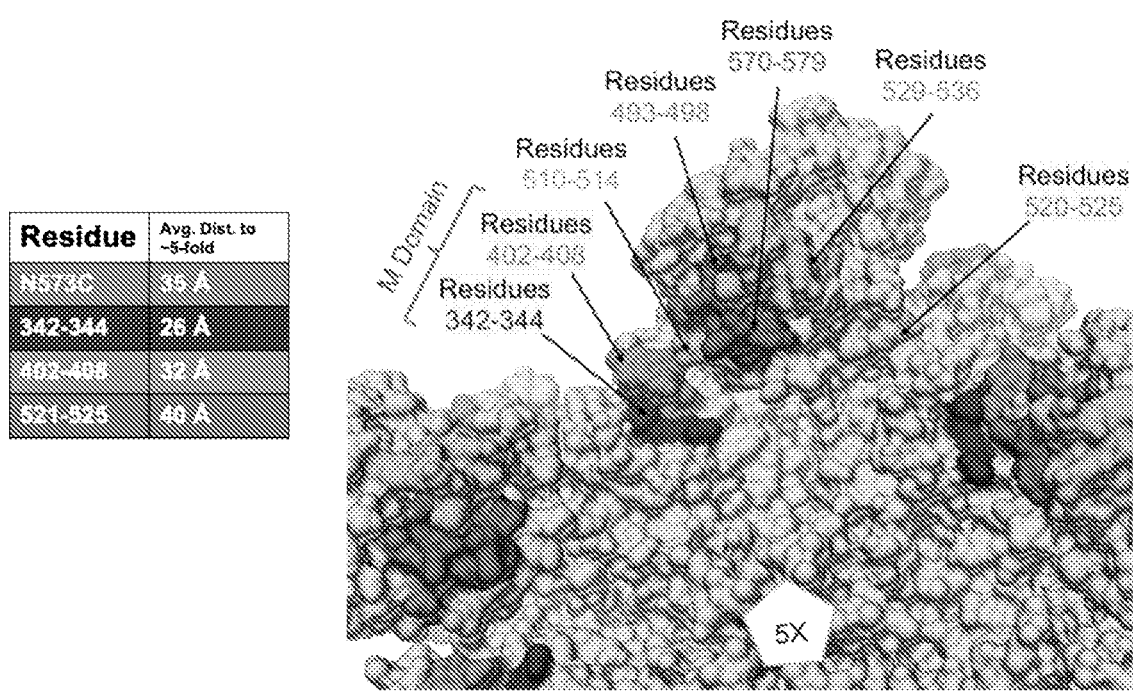

FIG. 17: Structure-based design of conjugation sites on the periphery of the P domain as well as the M domain, for the first time. Conjugation to these sites can be achieved through genetic engineering and/or chemical conjugation methods.

Figure 18:
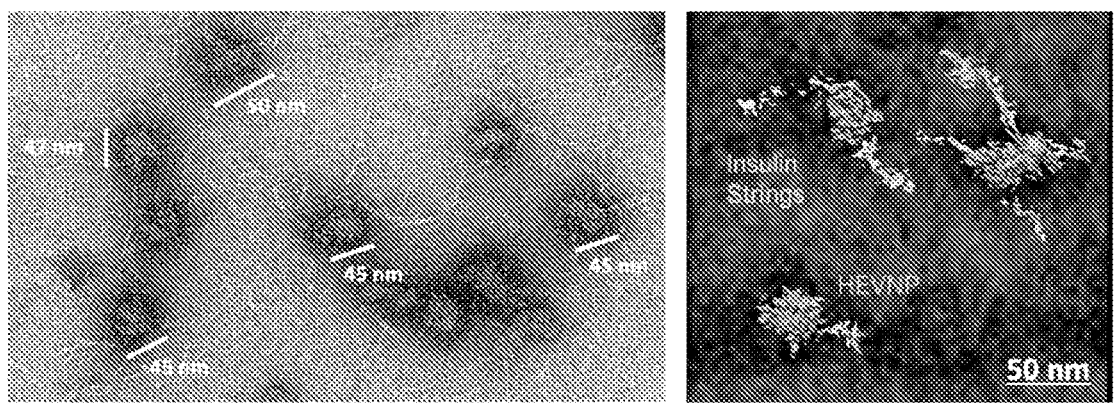

FIG. 18: Electron microscopy tomography reconstruction of insulin-detemir-encapsulated HEVNP (left TEM micrograph; right 3D reconstruction of the HEVNP and encapsulated insulin-detemir).

Figure 19:
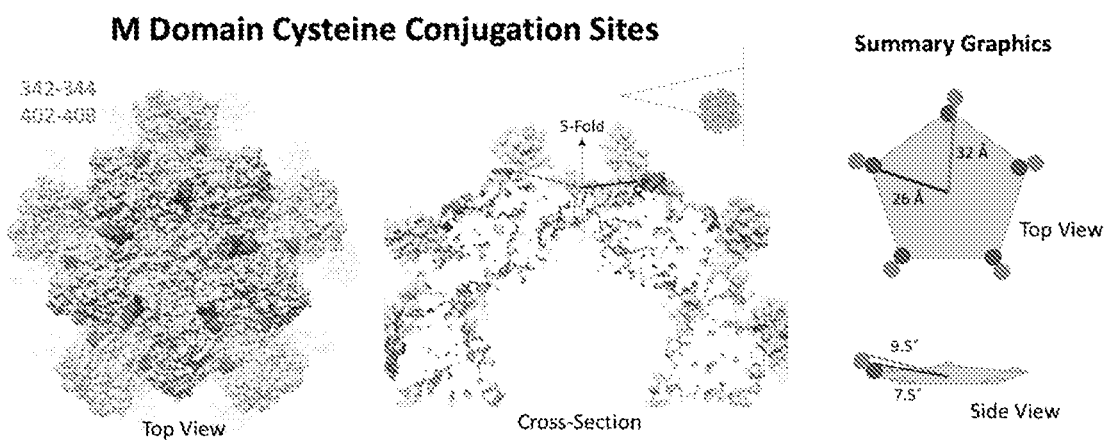

FIG. 19: M domain conjugations sites (residues 342-344 in blue & 402-408 in red). Geometrical measurements of the average distance and anchoring angle towards the 5-fold axis of HEVNP.

Figure 20:
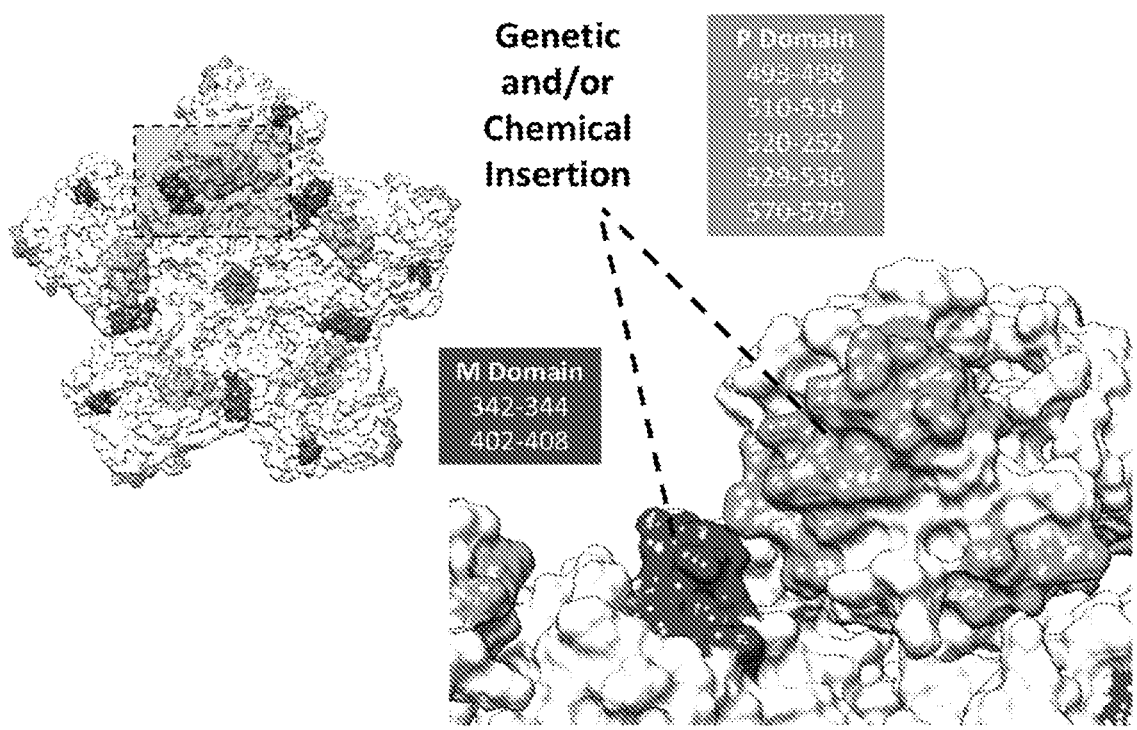

FIG. 20: Dual-insertion using both the M domain (blue) and the P domain (orange) sites to form conformational epitopes, through genetic and/or chemical insertions.

Figure 21A:
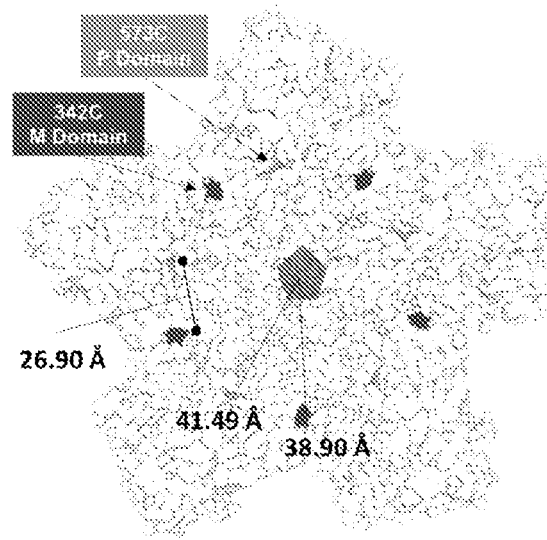
Figure 21B:
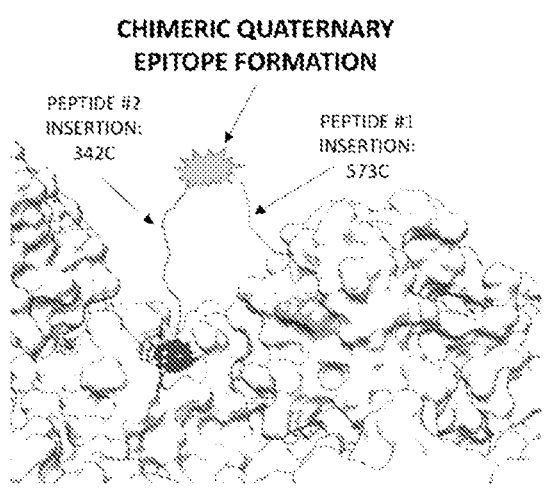

FIGS. 21A-21B: Detailed measurements of conjugation sites on the M domain (342C) and P domain (573C) to reveal distance between the two sites & their distance away from the center of the 5-fold axis. In FIG. 21B, illustration of 2 disparate peptide insertions on the P domain (orange) and the M domain (blue) to form a quaternary epitope.

Figure 22:
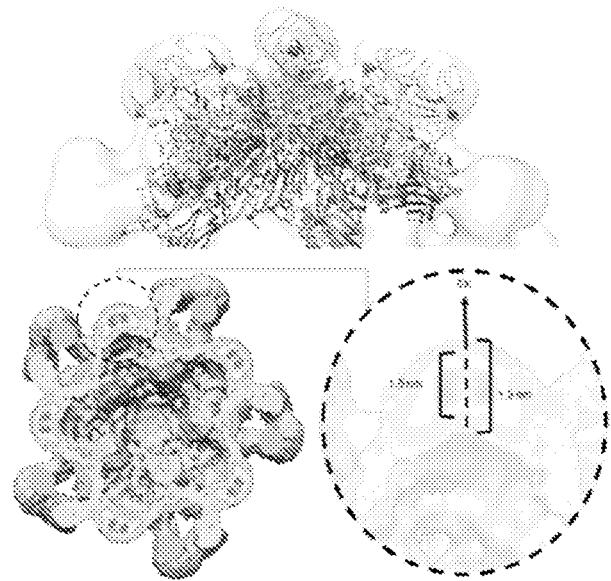
Figure 22:
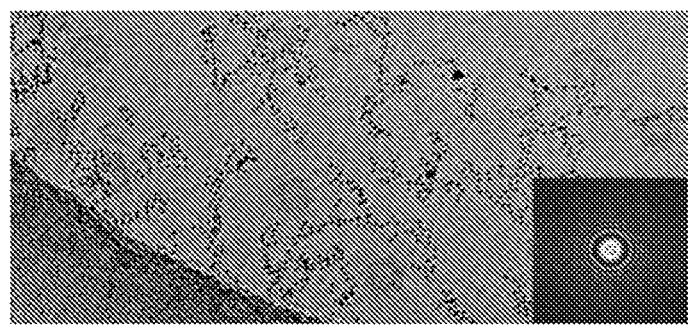
Figure 22:
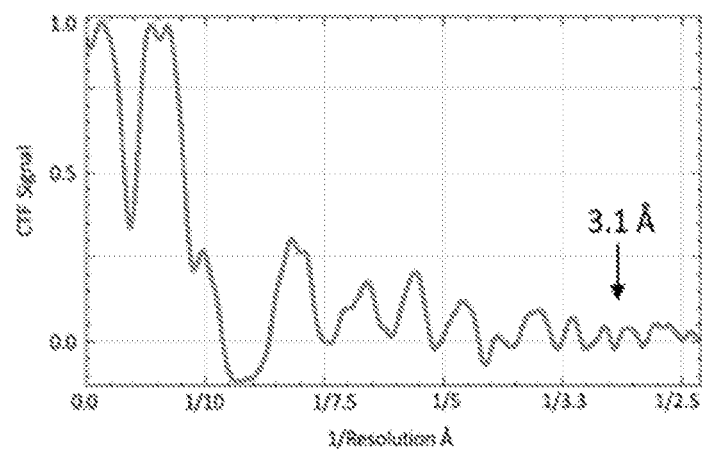

FIG. 22: Structure-guided modeling of the AuNC supercluster formation around the 5-fold axis of HEVNP, based on high-resolution 3D reconstruction using cryo-EM with direct electron detection technology.

Figure 23:
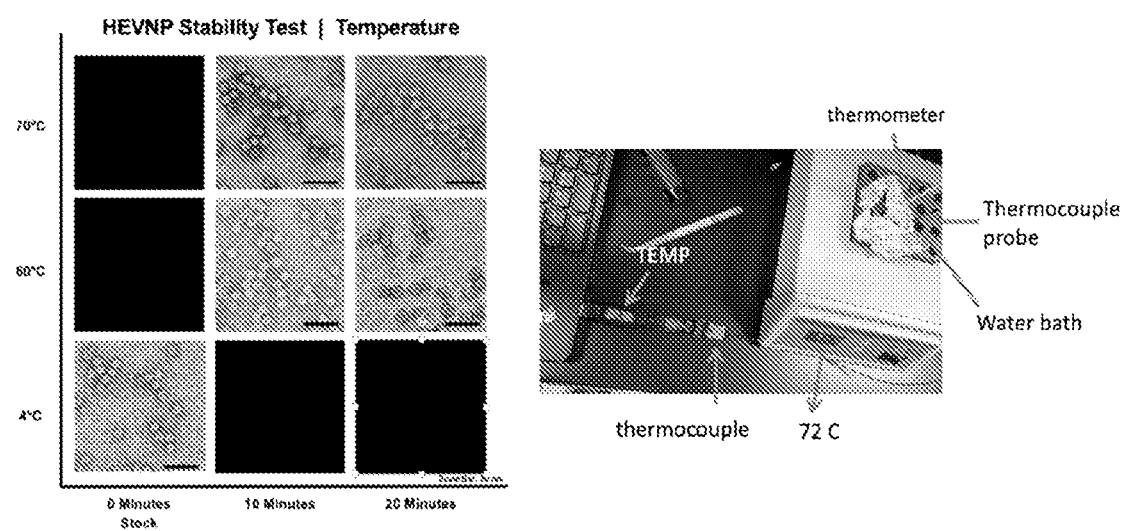

FIG. 23: Test of temperature tolerance of HEVNP post AuNC functionalization, showing that HEVN-AuNC can withstand temperatures as high as 70° C. over the duration of 20 minutes. On the right, experimental setup, using water bath and precise temperature measurements.

FIG. 24: Additional surface functionalization of HEVNP using beta-paired tag and catcher to enhance the surface modularity of HEVNP to carry larger proteins.

FIG. 25: Sequence alignment for all 6 versions of ORF2 (SEQ ID NO:1-6).

DEFINITIONS

As used in this specification and the appended claims, the singular forms "a," "an," and "the" include plural reference unless the context clearly dictates otherwise.

"Hepatitis E virus" or "HEV" refers to a virus, virus type, or virus class, which i) causes water-borne, infectious hepatitis; ii) is distinguished from hepatitis A virus (HAV), hepatitis B virus (HBV), hepatitis C virus (HCV), or hepatitis D virus (HDV) in terms of serological characteristics;

and iii) contains a genomic region that is homologous to a 1.33 kb cDNA inserted in pTZKF1(ET1.1), a plasmid embodied in a *E. coli* strain deposited in American Type Culture Collection (ATCC) with accession number 67717.

The terms "capsid protein" and "modified capsid protein," with reference to HEV, refer to a mature or modified (e.g., truncated, recombinantly mutated, or chemically derivatized) HEV open reading from 2 (ORF2) polypeptide. As used herein, reference to such ORF2 polypeptides or proteins is meant to include the full-length polypeptide, and fragments thereof, and also include any substitutions, deletions, or insertions or other modifications made to the ORF2 proteins. The capsid proteins must be capable of forming a virus like particle (VLP). Typically the capsid protein contains at least residues 112-608 of HEV ORF2, although the capsid protein can tolerate various additional substitutions, deletions, or insertions so long as they are tolerated without abrogating VLP formation.

In one embodiment, the term "modified capsid protein" refers to a capsid protein, or portion thereof (i.e., less than full length of the capsid protein), in which modifications such as one or more of additions, deletions, substitutions are present yet the resultant modified capsid protein remain capable of forming a VLP. These modifications include those described in U.S. Pat. Nos. 8,906,862 and 8,906,863, WO2015/179321. For instance, a heterologous polypeptide may be inserted into the capsid protein or a portion thereof, at locations such as within segment 483-490, 530-535, 554-561, 573-577, 582-593, or 601-603, or immediately after residue Y485, see U.S. Pat. Nos. 8,906,862 and 8,906,863. As an another example, WO2015/179321 describes further examples of modified capsid protein in which a surface variable loop of the P-domain of HEV ORF2 is modified to incorporate one or more cysteines or lysines that are not otherwise present in the wild-type capsid protein sequence. Alternatively, or additionally, the term "modified capsid protein" refers to a capsid protein, or portion thereof, in which at least one residue (e.g., position 342 or 573 or both) of HEV ORF2 is modified to incorporate one or more cysteines or lysines that are not otherwise present in the wild-type capsid protein sequence. Alternatively, or additionally, the term "modified capsid protein" refers to a capsid protein, or portion thereof, in which a cysteine or lysine (e.g., a cysteine or lysine of the S, M, or P-domain of HEV ORF 2 or a cysteine/lysine recombinantly introduced at position 342 or 573 or both) is chemically derivatized to covalently conjugate to the protein at least one heterologous atom or molecule. The cysteine or lysine can be inserted such that the HEV ORF2 protein length is increased, or the cysteine or lysine can replace one or more residues of an S, M, or P-domain surface variable loop and/or C-terminus.

Generally, modified capsid proteins retain the ability to form HEV VLPs. In some cases, the one or more cysteines or lysines are conjugated to a bioactive agent (e.g., a cell-targeting ligand such as the peptide LXY30). P-domain surface variable loops include one or more of, e.g., residues 475-493; residues 502-535; residues 539-569; residues 572-579; and residues 581-595 of HEV ORF 2 (SEQ ID NO:1, 2, 3, 4, 5, or 6). P-domain surface variable loops further include the residues of polypeptides comprising an amino acid sequence that is at least about 80%, 85%, 90%, 95%, 99%, or more identical to one or more of SEQ ID NOs:1, 2, 3, 4, 5, or 6 and that correspond to one or more of residues 475-493; residues 502-535; residues 539-569; residues 572-579; and residues 581-595 of SEQ ID NOs:1, 2, 3, 4, 5, or 6.

As used herein, the term "virus-like particle" (VLP) refers to an icosahedral shell (e.g., T1 or T3) formed by a capsid protein. VLPs are not infectious due to the lack of a viral genome. "VLP" refers to a nonreplicating icosahedral viral shell, derived from hepatitis E virus capsid protein HEV ORF2, a portion thereof. VLPs can form spontaneously upon recombinant expression of the protein in an appropriate expression system. In some embodiments, the VLP is formed from a modified capsid protein, e.g., a capsid protein containing one or more cysteine/lysine residues in a surface variable loop of HEV ORF2, or a portion thereof. An HEV VLP can contain a mixture of modified and/or unmodified HEV ORF2 proteins.

The term "acid and proteolytically stable" in the context of an HEV VLP refers to an HEV VLP that is resistant to the acid and proteolytic environments of a mammalian digestive system. Methods of assessing acid and proteolytic stability are described in Jariyapong et al., 2013, and include, but are not limited to subjecting an HEV VLP to an acid (e.g., pH of, or of about, 6, 5.5, 5, 4.5, 4, 3.5, 3, 2.5, or 2) and/or proteolytic environment (e.g., trypsin and/or pepsin) and examining the contacted HEV VLP by electron microscopy, gel filtration chromatography, or other suitable method to determine whether the quaternary structure (e.g., T=1, T=3, icosahedron, dodecahedron, etc.) of the HEV VLP is retained. A population of HEV VLPs (e.g., modified or unmodified) can be incubated under acid and/or proteolytic conditions for a suitable period of time (e.g., for at least, or for at least about, 1, 2, 3, 4, 5, 10, 15, 20, 30, 45, or 60 minutes) and then tested to determine the extent of quaternary structure retention. In this context, an acid and proteolytically stable modified HEV VLP refers to a modified HEV VLP that when incubated as a population of VLPs under acid and/or proteolytic conditions and assayed by electron microscopy, at least 10%, 25%, 50%, 75%, 90%, 95%, 99%, or 100% of the VLPs of the population retain their quaternary structure.

Alternatively, the HEV VLP can be delivered to a subject via an oral route and the efficiency of delivery assessed by detecting and/or quantifying: (i) an immune response to an antigen within the HEV VLP; (ii) a detectable label conjugated to, recombinantly introduced into, or encapsulated by the HEV VLP; or (iii) a biological response due to delivery to a cell of a bioactive agent associated with (e.g., recombinantly introduced into, conjugated to, or encapsulated by) the REV VLP. In this context, an acid and proteolytically stable modified HEV VLP refers to a modified HEV VLP that retains at least 10%, 25%, 50%, 75%, 90%, 95%, 99%, or 100% of the oral delivery efficacy and/or cell entry activity of an unmodified HEV VLP.

The term "heterologous" as used in the context of describing the relative location of two elements, refers to the two elements such as nucleic acids (e.g., promoter or protein encoding sequence) or proteins (e.g., an HEV ORF2 protein, or portion thereof, or modified capsid protein and another protein) that are not naturally found in the same relative positions. Thus, a "heterologous promoter" of a gene refers to a promoter that is not naturally operably linked to that gene. Similarly, a "heterologous polypeptide" or "heterologous nucleic acid" in the context of an HEV VLP or HEV capsid protein is one derived from a non-HEV origin.

Hepatitis E virus (HEV) is known to cause severe acute liver failure. HEV belongs to the genus Hepevirus in the family Hepeviridae. HEV contains a single-stranded positive-sense RNA molecule of approximately 7.2-kb. The RNA is 3' polyadenylated and includes three open reading frames (ORF). ORF1 encodes viral nonstructural proteins, located in the 5' half of the genome. ORF2 encodes a protein-forming viral capsid, located at the 3' terminus of the genome. ORF3 encodes a 13.5-kDa protein, overlapped with C-terminus of ORF1 and N-terminus of ORF2. ORF3 is associated with the membrane as well as with the cytoskeleton fraction.

The term "encapsulation," or "encapsulated," as used herein refers to the envelopment of a heterologous substance, such as a heterologous nucleic acid or protein, a chemotherapeutic, an imaging agent, a ferrite nanoparticle etc., within the VLPs defined herein.

The term "bioactive agent" refers to any agent, drug, compound, or mixture thereof that targets a specific biological location (targeting agent) and/or provides some local or systemic physiological or pharmacologic effect that can be demonstrated in vivo or in vitro. Non-limiting examples include drugs, hormones, vaccines, antibodies, antibody fragments, vitamins and co factors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, DNA, cDNA, antisense constructs, ribozymes, etc.).

A "pharmaceutically acceptable" or "pharmacologically acceptable" material is one that is not biologically harmful or otherwise undesirable, i.e., the material may be administered to an individual along with the capsid protein or the HEV VLPs or the compositions of the present invention without causing any undesirable biological effects. Neither would the material interact in a deleterious manner with any of the components of the composition in which it is contained.

The term "excipient" refers to any essentially accessory substance that may be present in the finished dosage form of the composition of this invention. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

The term "adjuvant" refers to a compound that, when administered in conjunction with an antigen, augments the immune response to the antigen, but does not generate an immune response to the antigen when administered alone. Adjuvants can augment an immune response by several mechanism including lymphocyte recruitment, stimulation of B and/or T cells, and stimulation of macrophages.

An "immunogenic response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is a heterologous moiety attached to a probe or a molecule with defined binding characteristics (e.g., a polypeptide with a known binding specificity or a polynucleotide), so as to allow the presence of the probe/molecule (and therefore its binding target) to be readily detectable. The heterologous nature of the label ensures that it has an origin different from that of the probe or molecule that it labels, such that the probe/molecule attached with the detectable label does not constitute a naturally occurring composition.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of HEV nanoparticle (HEVNP) encapsulating insulin is the amount of said HEVNP to achieve a detectable effect, such that the symptoms, severity, and/or recurrence chance of a target disease (e.g., diabetes) are reduced, reversed, eliminated, prevented, or delayed of the onset in a patient who has been given the HEVNP for therapeutic purposes. An amount adequate to accomplish this is defined as the "therapeutically effective dose." The dosing range varies with the nature of the therapeutic agent being administered and other factors such as the route of administration and the severity of a patient's condition. The word "about" as used herein denotes a range of +/−10% of a reference value.

The term "patient" as used herein refers to a vertebrate animal, e.g., of avian or mammalian species, especially a mammal (for example, a bull/cow, pig, sheep/goat, horse, rabbit, rodent, dog, cat, fox, etc.) including a primate such as a chimpanzee, a monkey or a human.

DETAILED DESCRIPTION OF THE INVENTION

A. Introduction

This disclosure relates to a viral-based nanocapsid HEVNP, which has at least one cysteine inserted into the ORF2 capsid protein sequence. The cysteine is then chemically derivatized and serves as an anchor to conjugate gold nanocluster to the HEVNP. The resultant HEVNP is chemically stable and resistant to the enzymatic activities or pH in the gastrointestinal tract, suitable for oral delivery of a pre-selected nucleic acid or protein (e.g., insulin).

The Hepatitis E Virus nanoparticle (HEVNP) is derived from a self-assembling, noninfectious nanocapsids. HEVNP is stable in acidic environment and resistant to proteolytic digestion, thus it possesses a great advantage as an oral delivery vehicle. HEVNP can be orally administered, then transported to the small intestine and ultimately to the target tissue/cells (e.g., liver) following HEV's natural transmission route. With its in vitro disassembly/reassembly ability, HEVNP is capable of encapsulating drug or nucleic acids to deliver them through the digestion system in gastrointestinal tract. The specific targeting ligand (e.g., a ligand targeting delivery to the liver) can be linked to the protrusion domain of HEVNP either by genetic engineering or chemical conjugation. The HEVNP structure is stabilized by conjugating monodispersed gold nano-clusters (AuNCs) for better bioavailability of oral delivered drug (e.g., insulin).

The specific aspects in this disclosure and earlier publications by the present inventors (see, e.g., U.S. Pat. Nos. 8,906,862 and 8,906,863, WO2015/179321) outline HEVNP production as well as methods and applications in surface modification, encapsulation for oral delivery of a nucleic acid or protein of therapeutic activity.

The structure stabilized HEVNPs as oral delivery capsule provides the following benefits: (1) eliminating needles, associated risks, and disposal requirements; (2) a therapeutic protein or a polynucleotide coding sequence itself, can be readily encapsulated into the HEVNP structure in vitro and delivered by oral ingestion; (3) HEVNP, composed of capsid proteins, can be biodegraded through protein degradation pathway with little toxicological concerns.

B. Production and Purification of Modified Capsid Proteins and VLP Formation

One aspect of the invention relates to methods for production and purification of capsid proteins and VLPs derived therefrom (See, Expression and self-assembly of empty virus-like particles of hepatitis E virus. Li T C, Yamakawa Y, Suzuki K, Tatsumi M, Razak M A, Uchida T, Takeda N, Miyamura T., J Virol. 1997 October; 71(10):7207-13. Essential elements of the capsid protein for self-assembly into empty virus-like particles of hepatitis E virus. Li T C, Takeda N, Miyamura T, Matsuura Y, Wang J C, Engvall H, Hammar L, Xing L, Cheng R H. J Virol. 2005 October; 79(20):12999-3006. Niikura M et al, Chimeric recombinant hepatitis E virus-like particles as an oral vaccine vehicle presenting foreign epitopes. Virology 2002; 293: 273-280). In one embodiment, the capsid proteins are modified capsid proteins and the VLPs derived therefrom are cysteine/lysine modified HEV VLPs. For example, the modified capsid proteins contain one or more cysteine/lysine residues in a surface variable loop of HEV ORF2, or a portion thereof.

Various expression systems can be used to express the capsid proteins of the present invention. Examples of expression systems useful for the production of virus-like particles of the present invention include, but are not limited to, bacterial expression system (e.g., E. coli), insect cells, yeast cells and mammalian cells. Preferred expression system of the present invention includes baculovirus expression systems using insect cells. General methods, for example, for handling and preparing baculovirus vectors and baculoviral DNA, as well as insect cell culture procedures, are outlined in A Manual of Methods for Baculovirus Vectors and Insect Cell Culture Procedures.

The capsid proteins of the present invention can be cloned into the baculovirus vector, and used to infect appropriate host cells (see, for example, O'Reilly et al., "Baculovirus Expression Vectors: A Lab Manual," Freeman & Co. 1992.). An insect cell line (e.g., Sf9 or Tn5) can be transformed with a transfer vector containing polynucleic acids which encodes the capsid proteins of the invention. The transfer vector includes, for example, linearized baculovirus DNA and a plasmid containing the desired polynucleotides. The host cell line may be co-transfected with the linearized baculovirus DNA and a plasmid in order to make a recombinant baculovirus.

Purification of the virus-like particles of the present invention can be carried out according to the standard technique in the art (See, Li T C, et al., J Virol. 1997 October; 71(10):7207-13. Li T C, et al., J Virol. 2005 October; 79(20):12999-3006. Niikura M et al, Virology 2002; 293: 273-280). The purified VLPs are then resuspended in a suitable buffer.

In some embodiments, the modified capsid proteins or VLPs derived therefrom can be chemically conjugated to one or more bioactive agents. For example, one or more cysteine/lysine residues of the capsid proteins can be acylated, alkylated, arylated, succinylated, or oxidized using methods known in the art. In some cases, the one or more cysteine/lysine residues can be conjugated using a maleimide functional group to covalently conjugate a bioactive agent to the thiol moiety of the cysteine or lysine. In some cases, the bioactive agent can be modified to introduce a maleimide functional group using CLICK chemistry. For example, an alkyne derivative of the bioactive agent can be contacted with a maleimide-azide in the presence of $CuSO_4$ and ascorbic acid to produce a maleimide bioactive agent. The maleimide can then be contacted with the one or more cysteines/lysines of the modified capsid protein to covalently link the two molecules. In some cases, the conjugating is performed on capsid protein that is not assembled into a VLP (e.g., in the presence of EDTA, EGTA, and/or a reducing agent such as DTT or betamercaptoethanol). In some cases, the conjugating is performed on capsid protein that is assembled into a VLP.

C. Encapsulation of Bioactive Agents

Another aspect of the invention relates to the encapsulation of one or more bioactive agents in HEV virus-like particles (e.g., cysteine modified, gold nanocluster conjugated HEV VLPs) (See, DNA vaccine-encapsulated virus-like particles derived from an orally transmissible virus stimulate mucosal and systemic immune responses by oral administration, Gene Therapy 2004. 11, 628-635. S Takamura, M Niikura, T-C Li, N Takeda, S Kusagawa, Y Takebe, T Miyamura and Y Yasutomi). Any standard technique in the art can be used to encapsulate a heterologous nucleic acid, protein, polypeptide, chemotherapeutic, imaging agent, nanoparticle, etc. into the VLPs of the present invention. An exemplary bioactive agent is insulin, either in the protein form or in the nucleic acid form. The general procedure involves (1) disassembling the VLPs formed by the capsid protein according to the present invention; and (2) reconstructing the VLPs in the presence of the bioactive agent. A skilled artisan would recognize that it is preferred to have purified VLPs before the encapsulation procedure. It is particularly preferred to have the VLPs depleted of, or substantially depleted of, any undesired materials (e.g., nucleic acids) before the encapsulation procedure.

Disassembly of VLPs can be carried out using any standard technique in the art. Reconstituted virus-like particle can be produced under physiological conditions (See, US Patent Publication No.: 20080131928). Often, disassembly of virus-like particles requires an agent to disrupt the assembly of VLPs, such as a reducing agent or a chelating agent (See, US Patent Publication No.: 20040152181). A skilled artisan would recognize that factors and conditions that affect assembly and disassembly include: pH, ionic strength, posttranslational modifications of viral capsid proteins, disulfide bonds, and divalent cation bonding, among others. For example, the importance of cation bonding, specifically calcium, in maintaining virion integrity has been shown for polyomavirus (Brady et al., J. Virol, 23:717-724, 1977), and rotovirus (Gajardo et al., J. Virol, 71:2211-2216, 1997). Also, disulfide bonds appear to be significant for stabilizing polyomavirus (Walter et al., Cold Spring Har Symp. Quant. Biol, 39:255-257, 1975; Brady et al., J. Virol, 23:717-724, 1977); and SV40 viruses (Christansen et al., J. Virol, 21:1079-1084, 1977). Also, it is known that factors such as pH and ionic strength influence polyomavirus capsid stability, presumably by affecting electrostatic interactions (Brady et al., J. Virol, 23:717-724, 1977; Salunke et al., Cell, 46:895-904, 1986; Salunke et al., Biophys. J, 56:887-900, 1980). Also, it is known that post-translational modifications of some viral capsid proteins may affect capsid stability and assembly, e.g., glycosylation, phosphorylation, and acetylation (Garcea et al., Proc. Natl. Acad. Sci. USA, 80:3613-3617, 1983; Xi et al., J. Gen. Virol, 72:2981-2988, 1991). Thus, there are numerous interrelated factors which may affect capsid stability, assembly and disassembly.

Preferably, the VLPs of the present invention is disassembled by the removal of calcium ions (See, Touze A, Coursaget P. In vitro gene transfer using human papillomavirus-like particles. Nucleic Acids Res 1998; 26:1317-1323; Takamura et al., DNA vaccine-encapsulated virus-like particles derived from an orally transmissible virus stimulate mucosal and systemic immune responses by oral administration. Gene Therapy 2004; 11:628-635). According to the present invention, a reducing agent or a chelating agent or both are used to disassemble the VLPs. Various reducing agents can be used. Preferred embodiments of the reducing agents include, but are not limited to, dithiothreitol (DTT). Various chelating agents can be used, e.g., ethylene glycol tetraacetic acid (EGTA) or ethylenediaminetetraacetic acid (EDTA). Examples of VLP disassembly conditions include, but are not limited to, the following: purified VLPs were disrupted by incubation of a buffer containing 50 mM Tris-HCl (pH 7.5), 150 mM NaCl, 1 mM EGTA and 20 mM dithiothreitol for 30 minutes.

A skilled artisan would also recognize that complete disassembly of the VLPs is not required, although preferred, to encapsulate a bioactive agent. An artisan would also recognize that, on other occasions, it is preferred to have partial disassembly of the VLPs. According to the present invention, the conditions for the partial disassembly of the VLPs can be controlled to still allow efficient encapsulation of a bioactive agent. Partial disassembly of the VLPs can be achieved by treatment of VLPs with reducing agents alone (e.g., 20 mM DTT) (Sapp et al, J. Gen. Virol., 76:2407-2412, 1995.). According to the present invention, once the VLPs are disassembled completely or partially, encapsulation of a bioactive agent can be carried out by reassembling the VLPs in the presence of the bioactive agent. In some cases, it can be advantageous to utilize a bioactive agent having a net negative charge to enhance encapsulation. For example, nucleic acids have a net negative charge and can be preferentially encapsulated as compared to compounds that have a positive or neutral charge.

In some embodiments of the present invention, reassembly of the VLPs is achieved by re-supplementation of calcium ions to the disrupted VLPs. Alternatively, reassembly of the VLPs is achieved by removal of the reducing agents or the chelating agents. Optionally, factors such as pH and ionic strength, other factors described in the present invention, can be adjusted to achieve efficient reassembly of the VLPs and efficient encapsulation of the bioactive agent.

In some embodiments, encapsulation is performed as follows: following 30 min of incubation at room temperature, a bioactive agent in 50 mM Tris-HCl buffer (pH 7.5) and 150 mM NaCl is added to the disrupted VLP preparation. The disrupted VLP preparation is then refolded by incubation for 1 h with increasing concentrations of $CaCl_2$) up to a final concentration of 5 mM. VLPs are pelleted by ultracentrifugation and resuspended in 10 mM potassium-IVIES buffer (pH 6.2). To estimate the amounts of encapsulated agent, refolded and purified VLPs are purified from any unencapsulated bioactive agent and disrupted with EGTA (1 mM). Absorbance of the supernatant, or other suitable methods can be used for detection of the bioactive agent.

In some embodiments, the bioactive agent (e.g., a heterologous protein or nucleic acid such as insulin protein or insulin-encoding nucleic acid) or imaging agent to be encapsulated is conjugated to an encapsulation signal. For example, an RNA element corresponding to codons 35-59 of HEV open reading frame 1 is a powerful encapsidation signal, allowing specific interaction in vitro with HEV capsid protein, including truncated and/or cysteine/lysine modified versions of HEV ORF2 VLP as described herein. To use VLP as a carrier for therapeutic or imaging agents, chemical linkers (e.g., LC-SPDP or aptamer, telodendrimers) that tag the agent (e.g., chemotherapeutic) with an HEV encapsidation signal like the foregoing RNA element can be used prior to the capsid self-assembly.

In some embodiments, a detectable label (imaging agent) is encapsulated. The detectable label can be a moiety renders a molecule to which it is attached to detectable by a variety of mechanisms including chemical, enzymatic, immunological, or radiological means. Some examples of detectable labels include fluorescent molecules (such as fluorescein, rhodamine, Texas Red, and phycoerythrin) and enzyme molecules (such as horseradish peroxidase, alkaline phosphatase, and β galactosidase) that allow detection based on fluorescence emission or a product of a chemical reaction catalyzed by the enzyme. Radioactive labels involving various isotopes, such as $^3H$, $^{125}I$, $^{35}S$, $^{14}C$, or $^{32}P$, can also be attached to appropriate molecules to enable detection by any suitable methods that registers radioactivity, such as autoradiography. See, e.g., Tijssen, "Practice and Theory of Enzyme Immunoassays," Laboratory Techniques in Biochemistry and Molecular Biology, Burdon and van Knippenberg Eds., Elsevier (1985), pp. 9 20. An introduction to labels, labeling procedures, and detection of labels can also be found in Polak and Van Noorden, Introduction to Immunocytochemistry, 2d Ed., Springer Verlag, N Y (1997); and in Haugland, Handbook of Fluorescent Probes and Research Chemicals, a combined handbook and catalogue published by Molecular Probes, Inc. (1996). Further detectable labels include, but are not limited to, superparamagnetic labels (e.g., ferrite), contrast enhancing reagents (e.g., MRI contrast agents), atom-clusters (e.g., gold clusters), and the like. The conjugation of monodispersed gold cluster onto the modified capsid protein, e.g., onto cysteine/lysine residue(s) including the artificially introduced cysteine/lysine residue(s) in the modified capsid protein, can be performed according to the methods known in the art and described in various publications.

In some embodiments, a bioactive agent is encapsulated. In some cases, the bioactive agent is a chemotherapeutic. Suitable chemotherapeutics include, but are not limited to, cytotoxic drugs. Examples of cytotoxic drugs which may be used in the present invention include: alkylating drugs, such as cyclophosphamide, ifospfamide, ehlorambucil, melphalan, busulfan, lomustine, carmustine, chlormethhine (mustine), estramustine, treosulfan, thiotepa, mitobronitol; cytotoxic antibiotics, such as doxorubicin, epirubicin, aclarubicin, idarubicin, daunorubicin, mitoxantrone (mitozantrone), bleomycin, dactinomycin and mitomycin; antimetabolites, such as methotrexate, capecitabine; cytarabine, fludarabine, cladribine, gemcitabine, fluorouracil, raltitrexed (tomudex), mercaptopurine, tegafur and tioguaninc; vinca alkaloids, such as vinblastine, vincristine, vindesine, vinorelbine and etoposide; other neoplastic drugs, such as amsacrine, altetarmine, crisantaspase, dacarbazine and temozolomide, hydroxycarbamide (hydroxyurea), pentostatin, platinum compounds including: carboplatin, cisplatin and oxaliplatin, porfimer sodium, procarbazine, razoxane; taxanes including: docetaxel and paclitaxel; topoisomerase I inhibitors including inotecan and topotecan, trastuzumab, and tretinoin. In some cases, one or more of the foregoing imaging agents and/or bioactive agents, or a combination thereof, can additionally or alternatively be conjugated to a cysteine or lysine (e.g., recombinantly introduced cysteine or lysine) in a P-domain surface variable loop or C-terminus via a thiol linkage. In some cases, one or more of the foregoing imaging agents and/or bioactive agents, or a combination thereof, can additionally or alternatively be conjugated to a second cysteine or lysine (e.g., recombinantly introduced cysteine or lysine) in a P-domain surface variable loop or C-terminus via a thiol linkage.

In some embodiments, insulin is the bioactive agent encapsulated in the HEV VLP construct of this invention. Insulin in the form of a biologically active polypeptide (which may include optional post-translational modification, such as glycosylation, PEGylation, or substitution of one or more artificial amino acid analogues including D-amino acids, etc.) is used in some cases, whereas in other cases, insulin is in the form of a polynucleotide sequence (e.g., cDNA) encoding the insulin and/or proinsulin protein, for example, the insulin-encoding nucleic acid is a human insulin gene expression construct in a TA1m vector[12]. The insulin protein may be recombinant or it may be isolated from a natural source. It may be a human insulin or derived from other animals such as bovine, porcine, feline, or canine animals. It may be proinsulin. Different forms of insulin can be used: rapid-acting (Aspart: Novolog; Glulisine; Apidra; Lispro: Humalog); short-acting (Regular: Humulin, Humulin R, Novolin); intermediate-acting (NPH: Humulin N, Novolin N); intermediate to Long-acting (Detemir); long-acting (e.g., Glargine). Furthermore, the bioactive agent may be an analogue of insulin, such as a commercial insulin analog marketed as Levemir; or insulin glargine, which is a long-acting basal insulin analogue and marketed under the names Lantus. Additionally, the bioactive agent may be a combination of an insulin and glucagaon like peptide (GLP-1) receptor or other drugs. Examples of GLP-1 receptor agonists include liraglutide (Victoza, Saxenda), lixisenatide (Lyxumia), albiglutide (Tanzeum), dulaglutide (Trulicity), and semaglutide (Ozempic). Suitable forms or combinations of insulin include but are not limited to insulin glargine; insulin lispro; insulin aspart; insulin detemir; insulin (human); insulin aspart+insulin aspart protamine; insulin glulisine; insulin (human)+insulin isophane [INN]; insulin aspart+insulin degludec; insulin aspart+insulin isophane [INN]; insulin degludec+liraglutide; insulin glargine+lixisenatide; insulin human+insulin isophane [INN]; insulin isophane [INN]+insulin neutral; insulin isophane human [INN]+insulin human; insulin (bovine); insulin degludec; insulin human zinc; insulin isophane [INN]; insulin isophane human [INN]; insulin neutral; insulin human+insulin isophane human [INN]; insulin neutral+insulin isophane [INN]; insulin (porcine); insulin, neutral; protamine zinc insulin; insulin; insulin tregopil [INN]; insulin human+proinsulin human; insulin glargine+insulin lispro; insulin human+pramlintide acetate; dulaglutide; dulaglutide+insulin glargine; exenatide+insulin lispro; insulin glargine+liraglutide; insulin lispro+pramlintide; efpeglenatide [INN]; insulin human+pramlintide; exenatide+insulin human; insulin lispro+insulin lispro protamine; clioquinol [INN]+insulin human; insulin glargine+insulin glulisine; and insulin I 131. Further, various peptidyl and non-peptidyl insulin mimetics such as those described in by Nankar et al. (*Drug Discovery Today*, Volume 18, Issues 15-16, August 2013, Pages 748-755) may be used as bioactive agents for encapsulation in HEV VLPs.

The size of the VLPs can vary when different constructs of the capsid protein are used. For example, the N-terminal portion of the capsid protein can be adjusted to increase or decrease the size and encapsulation capacity of the VLPs. In some embodiments of the invention, in constructing the HEV VLP, a portion of HEV ORF 3 protein fused to the N-terminal of a portion of HEV ORF 2 proteins is utilized to adjust the size of the VLPs. Typically, the HEV VLP is formed from a portion of HEV ORF2 having at least residues 112-608 of HEV ORF 2.

D. Pharmaceutical Compositions, Formulations, and Administration

The present invention also provides pharmaceutical compositions or physiological compositions comprising an HEVNP formed by a modified capsid protein conjugated with a gold nanocluster encapsulating a bioactive agent (e.g., a heterologous nucleic acid or protein). Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery. See Langer, *Science* 249: 1527-1533 (1990).

The compositions of the present invention can be administered to a host with an excipient. Excipients useful for the present invention include, but are not limited to, vehicles, binders, disintegrants, fillers (diluents), lubricants, glidants (flow enhancers), compression aids, colors, sweeteners, preservatives, suspending/dispersing agents, film formers/coatings, flavors and printing inks.

One advantage of the present invention is that the compositions of the present invention are suitable for oral delivery. Because the HEVNP of this invention is highly stable in an acidic environment and resistant to digestion in the gastrointestinal tract, it is suitable for oral delivery of insulin. The gold nanocluster conjugated to the cysteine or lysine residue(s), especially those engineered into the surface of a modified capsid protein in some embodiments of the present invention, further enhances the stability, bioavailability, and delivery efficiency of the HEVNP. Thus, oral delivery of the compositions of the present invention can effective provide therapeutic benefits for patients in need of treatment by the encapsulated bioactive agent (e.g., insulin protein or DNA encoding insulin). The HEVNP of this invention may be formulated in the form of a solid (e.g., powder) or a liquid such that it may be used as a supplement to ordinary food or beverage items for consumption in daily life.

Additionally, the compositions of the present invention may also be formulated for mucosal delivery, such as delivery to the buccal or labial mucosa or the respiratory tract mucosa, including the nasal mucosa.

The pharmaceutical compositions of the present invention can be administered by various routes, e.g., oral, subcutaneous, transdermal, intradermal, intramuscular, intravenous, or intraperitoneal. The preferred routes of administering the pharmaceutical compositions are oral delivery at daily doses of about 0.01-5000 mg, preferably 5-500 mg, of the HEVNP. Oral administration is a preferred mode of administration, and the appropriate dose may be administered in the form of tablets, capsules, or as a supplement to food or beverage items in a single daily dose or as divided doses presented at appropriate intervals, for example as two, three, four, or more subdoses per day.

For preparing pharmaceutical compositions of the present invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an HEVNP of this invention with an encapsulated nucleic acid. In tablets, the active ingredient (an HEVNP with an encapsulated nucleic acid) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound with encapsulating material as a carrier providing a capsule in which the active component (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a chimeric virus-like particles with an encapsulated nucleic acid) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like. It is also expected that the HEVNP may be in the form of tablets/capsules in prepackaged powder or concentrated liquid form as sold. This would be further added into food or beverage including water by the patient and then consumed by the patient. The HEVNP can also be in liquid form and directly consumed without further dilution.

Sterile solutions can be prepared by suspending the active component (e.g., an HEVNP with an encapsulated nucleic acid) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 9, more preferably from 5 to 8, and most preferably from 6 to 7.

The pharmaceutical compositions of the present invention can be administered for prophylactic and/or therapeutic treatments. In therapeutic applications, compositions are administered to a patient already suffering from a condition in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the composition per day for a 70 kg patient, with dosages of from about 5 mg to about 500 mg of the composition per day for a 70 kg patient being more commonly used.

In prophylactic applications, pharmaceutical compositions of the present invention are administered to a patient susceptible to or otherwise at risk of developing a disease or condition, such as diabetes, in an amount sufficient to delay or prevent the onset of the symptoms. Such an amount is defined to be a "prophylactically effective dose." In this use, the precise amounts of the composition again depend on the patient's state of health and weight, but generally range from about 0.1 mg to about 2,000 mg of the inhibitor for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of composition of the present invention sufficient to achieve an intended effect in the patient, either therapeutically or prophylactically.

EXAMPLES

The following examples are provided by way of illustration only and not by way of limitation. Those of skill in the art will readily recognize a variety of non-critical parameters that could be changed or modified to yield essentially the same or similar results.

Example 1: Gold Nanocluster-Conjugated HEVNP

Introduction

The use of nanoparticles has been a central focus in nanotechnology and nanomedicine [1, 2]. Use of nanoparticles offer promising approaches to diagnosis, targeting, and treatment. Current approaches to battle cancer are limited to surgery, chemotherapy, and radiation [3]. While these methods are somewhat effective in diagnosis and treatment of cancerous regions, the lack of specificity in targeting hampers the efficiency of treatment and cause damage to healthy cells.

Among nanoparticles or nanoparticulate systems such as polymer-based, lipid-based, or dendrimers, a handful of protein-based capsids, derived from viruses, also known as virus-like particles (VLPs), have the lowest toxicity levels and highest bioavailability [4]. To date, several prophylactic VLPs have been approved by the FDA as commercialized vaccines. These include GlaxoSmithKline's Engerix® (hepatitis B virus) and Cervarix® (human papillomavirus), and Merck and Co., Inc.'s Recombivax HB® (hepatitis B virus) and Gardasil® (human papillomavirus) [5]. Other VLP-based vaccines are currently under clinical development against influenza virus, parvovirus, and Norwalk [5, 6]. The advances in VLP technology is not limited to vaccination; VLPs are also ideal candidates as drug carriers due to their high bioavailability [7, 8]. Recent advances in chemical surface modulation has promoted VLPs into capable multimodality vehicles for antigen, targeting ligand, and tracking molecules [9-12].

Hepatitis E nanoparticles (HEVNPs) have shown great promise in nucleic acid, and metabolic drug encapsulation, as well as surface modulation [11, 13]. Since by nature HEV infects via feco-oral routes, the protein capsid has gained the evolutionary advantage to survive the harsh acidic and enzymatic conditions of the GI tract, and therefore, the noninfectious nanoparticles derived from HEV can be readily utilized for oral and mucosal administration [14-17]. The technological achievements of HEVNP is summarized in review articles by Baikoghli et al. 2018 and Stark et al. 2016 [13]. Here we highlight and discuss the surface modulation of HEVNP in the context of tracking molecule surface modulation via AuNCs, and overall stability of the nanoparticle under different pH conditions.

Hepatitis E Nanoparticles (HEVNP)

Hepatitis E virus (HEV) is a positive sense single stranded RNA virus, with genome size of 7.2 kbp and diameter of 420 Å. Genetic modifications to the ORF2 of HEV, including 111 AA truncation to the N-terminus and 52 AA truncation to the C-terminus, results in the formation of smaller, genome-free HEV nanoparticles with diameter of ~270 Å [18, 19]. The structure of HEVNP has been resolved by x-ray crystallography [20]. HEVNPs retains the icosahedral stability of the virion when expressed in Baculovirus expression system using pOFR2 [19, 21]. There are sixty subunits, composed of three domains each, forming the icosahedral capsid of HEVNP (FIG. 1 A). The shell domain (S) (AA: 118-317) is critical in inter-subunit interactions, stabilizing the icosahedral capsid. The middle domain (M) (AA: 318-451) binds and interacts with the S domain [11, 22]. The protrusion domain (P) (452-606) forms a dimeric spike at the 2-fold axis. The M domain is connected to the P domain via a proline-rich hinge, which facilitates the topological changes in the protruding spikes [19, 21].

HEVNP's surface is composed of multiple anchoring sites repeated in the sixty identical subunits which can be modulated with various conjugates. Such modularity allows for easy conjugation of small peptides, tissue-targeting molecules, and tracking molecules such as fluorescent dye and gold nanoclusters. Moreover, in the bottom of the shell (S) domain, positively charged residues at the N-terminus, facing the interior surface of HEVNP, can be used for encapsulation of DNA, CRISPR RNA, and proteins. Exposed P domain loops (loops I (483-491), II (530-535), III (554-561), IV (582-593), and 573C) aid in targeting-ligand conjugation sites [11, 23]. The P domain of HEVNP surface is composed of multiple anchoring sites in each of the sixty identical subunits, which can be used for surface functionalization, without altering the icosahedral organization of the capsid protein [11, 15].

HEVNP Surface Modulation

Surface functionalization of nanoparticles is a critical step towards selective conjugation of naturally occurring and synthetic molecules. In 2013, Jariyapong et al. genetically inserted a highly immunogenic 15 residue peptide (p18), derived from the third hypervariable loop of HIV onto the surface of HEVNP [15]. Displaying 60 copies of p18, the chimeric HEVNP triggered a robust HIV-1-specific CTL response. The insertion, after the residue Tyr485 did not interfere with the icosahedral arrangement and overall stability of HEVNP. While has been proven to be a highly effective approach for mucosal vaccination, the conjugation method had its limitations; including a highly labor intensive chimeric-HEVNP production, repeatability, and duration of preparation [11, 13, 15].

In 2016, Chen and colleagues utilized thiol-ligand exchange approach to functionalize the surface of HEVNP. For surface conjugation on P domain, 5 cysteine replacement cites were selected; these include Y485, T489, Y533, N573, and T586. Of the five engineered sites, N573C was best suited for further modification. To this end, a breast cancer targeting ligand, LXY30 [24] was conjugated to the N573C site. As a proof of concept, in vivo studies carried out in mice showed that HEVNPs without LXY30 conjugation do not accumulate in tumor site, but LXY30 functionalized HEVNPs do. Compared to genetic modifications, chemical conjugation is a more efficient and highly reproducible method for surface functionalization [11].

Co-Localization of AuNCs Around the Icosahedral 5-Fold Axis of HEVNP

Subsequently, Stark and colleagues successfully conjugated magnetic nano-gold clusters, functionalized with pMBA44, a six carbon long spacer, and maleimide linker, (HEVNP+Au102C6MI from hereafter) to the 573C site on HEVNP (FIGS. 1 A & B) [25-27]. The structure, surface charge, and electronic and vibrational characteristics of Au102 have been extensively described [26, 28-30]. The HEVNP+Au102C6MI were purified and prepared for cryo-EM analysis. A comparative 2D analysis was carried out and unique, electron-dense regions were observed in the Au102C6MI conjugated HEVNPs (FIG. 1 C). Cryo-EM single particle analysis was carried out to achieve a 3D density map of the functionalized nanoparticles, as well as 573C-HEVNPs as control. From the collected datasets, a three-dimensional initial model was generated through an iterative de novo approach to determine and cross-validate particle parameters [31]. A robust PFT-based particle screening protocol was employed to determine particle orientation with respect to three angles phi, theta, and omega, as well as cartesian coordinates [32, 33]. Furthermore, using scale factor analysis integrated in PFT package, the particles were screened to reduce size heterogeneity [32]. Subsequently, 3D reconstruction and refinement was carried out (FIG. 1 D) [31, 34].

Figure 1D:
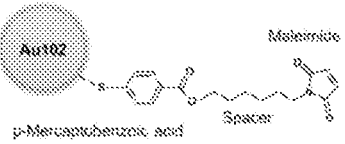
Figure 1E:
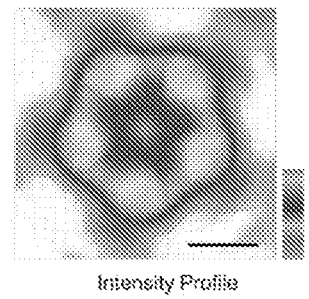

For validation and structural analysis via difference mapping, we carried out simultaneous 3D reconstruction on both control and HEVNP+Au102C6MI. In both reconstruction, the S, M, and P domains were clearly resolved (FIG. 1D). In addition, 2D and 3D image analysis of HEVNP+Au102C6MI revealed five unique high-density regions were present around the 5-fold axis in a doughnut-like array, that were not present in the control reconstruction; validated by difference mapping [25]. Local intensity analysis was performed to characterize the HEVNP+Au102C6MI 5-fold axis densities to confirm the size of Au102C6MI. It was shown that the addition of the C6 linker arm to the Au102 pMBA provides support for doughnut-like colocalization to stabilize around the 5-fold axis of HEVNP (FIG. 1 E). We hypothesized that such co-localization around the 5-fold axis of HEVNP may enhance the stability of the nanoparticle by increasing the stability of intramolecular interactions, supporting the decametric interface.

Impact of pH on the Stability of HEVNP

The highly compact intermolecular interface at the icosahedral 5-fold axis are critical for nanocapsid assembly and stability. Comprised of residues in S domain only, the decametric interactions at the 5-fold axis are tighter than those at the dimer and trimers at the 2-fold and 3-fold axes, respectively. There are 4 loops between the beta-sheets in the S domain; 2 out of the 4 loops are involved in intermolecular interactions with adjacent subunits. These interactions are mediated by side chains of Asn-200 and Tyr-288, which are separated by a distances of less than Angstroms [23, 35]. Site-mutation studies have revealed that these residues are critical for nanocapsid formation and stability. It is noteworthy to mention that similar 5-fold interactions mediated by aromatic amino acids such as Phe and Tyr are also observed in rNV (Recombinant Norwalk Virus), SMSV (San Miguel Sea Lion Virus), and CARMV (Carnation Mottle Virus); suggesting an evolutionary significance of 5-fold intermolecular interface in nanocapsid formation [23].

To test whether the enhanced stability of HEVNP via Au102C6MI is facilitated by colocalization around the 5-fold 184 icosahedral axis, we carried out pH stability experiments. It is previously reported that HEVNP is most stable at pH 6.2; at this optimal pH, the Ca+ bridge at the 3-fold axis and the intermolecular interactions at the 5-fold axis provide stability to the T=1 icosahedral protein capsid. At pH 8.0, HEVNP begins to swell, suggesting weakened intermolecular interfaces enforcing the compact T=1 icosahedral conformation. We carried out pH stability experimentation by incubating the HEVNPs in pH 6.2 and pH 8.0 buffers overnight. TEM imaging revealed a significant difference in size for the HEVNP nanoparticles in pH 6.2 (average diameter 23 nm), and pH 8.0 (average diameter 27 nm) (FIG. 2 A). To quantitatively describe our TEM observational analysis, the particles were subject to circular averaging to map out radial intensity analysis (FIG. 2 B). It was observed that particles at pH 8.0 are on average 10-15% larger than those in pH 6.2. Furthermore, molecular modeling was carried out to observe intermolecular interactions at the 5-fold axis under pH 6.2 and pH 8.0; the results suggest a weaker interface at pH 8.0 (FIG. 2 C). These results indicate that at pH 8.0, the HEVNP particles may have collapsed or the capsid protein stability is significantly weakened.

We hypothesized that structural preservation of the 5-fold intermolecular interface may play a critical role in the enhancement of HEVNP's stability at higher pH levels. After the HEVNP+Au102C6MI were incubated in pH 6.2 and pH 8.0 buffers overnight, TEM imaging revealed that the Au102C6MI conjugated HEVNPs did not increase in capsid size as a consequence of a weakened stability due to the relaxed interactions between the capsid subunits (FIG. 3A). Similarly, we carried out 2D circular averaging of the capsid projections to comparatively study the radial intensity profile of these particles. Unlike the control capsid without gold conjugates, we observed no significant changes of the capsid projection in radius (FIG. 3 B). These results indicate that the co-localization of the Au102C6MI around the 5-fold axis may reinforce intermolecular interactions at the S domain interface, and thus enhance the stability of HEVNPs at higher pH values.

Conclusion

Previously, cryo-EM SPR revealed that the Au102C6MI surface conjugation results in the formation of a doughnut-like ring around the 5-fold icosahedral axis of HEVNP [25]. The Au102 core is measured to be 1.5 nm, while the hydrodynamic diameter (including pMBA) measures to be about 2.5 nm. These dimensions fit well with the densities observed in the cryo-EM 3D reconstruction density map of HEVNP+Au102C6MI. The C6 spacer is about 1.1 nm, so the distance from the center of the gold core to the maleimide binding site (573C) is approximately 2-3 nm, all together. The length of the C6 arms is sufficient to provide enough flexibility for Au102C6MI colocalize around the 5-fold axis (FIG. 3 C-E). Here, we demonstrated that the conjugation of Au102C6MI enhances the overall stability of HEVNP at pH 8.0; whereas the control HEVNP particles show an increase in overall size, and weakened compactness at pH 8.0.

The trend towards the usage of nanoparticulate systems has gravitated tremendous attention in the nanomedicine field. The composition and reproducibility of nanoparticle systems is critical in the context of nanodelivery systems. Furthermore, the effectiveness of nanoparticle systems in nanomedicine is governed by bioavailability and compatibility with physiological conditions. As such, hepatitis E nanoparticles have shown considerable potential in encapsulation of nanotheranostics and surface modulation. The applications of such protein-based platform ranges from tissue-specific delivery of drugs, nucleic acids, and inorganic metals, to surface modulation for mucosal vaccination, cancer theranostics, and particle tracking.

The enhanced stability of HEVNP demonstrated in this report can be beneficial towards particle tracking studies. While, highly sensitive fluorescence microscopy techniques allow single nanoparticle tracking during the uptake into living cells [37], a higher spatial resolution in sub-nm range can be achieved by TEM. Utilizing the uniform electron dense Au102C6MI [27, 38], electron microscopic studies can be carried out to further our understanding of the distribution of particles in targeted tissues and their specific interactions with cells; Cryo-fixation and chemical fixation techniques can be employed to process tissues in resin blocks and subsequently sectioned by ultramicrotomy for 2D and 3D studies by transmission electron microscopy [39, 40].

In context of tumor-targeted hyperthermia treatment, enhanced stability of HEVNP via Au102C6MI conjugation may serve as an advantage in electromagnetic field enhancement of the radiative properties of Au102 [41]. It has been reported that strong local surface plasmon resonance develops in AuNC protected by thiolate monolayer [42]. Moreover, if the Au nanoparticles are small enough (ranging between 1.5-3.0 nm in diameter), strong plasmon resonance occurs with the gold at wavelengths ranging between 520-540 nm [42, 43]. Laser-induced tissue hyperthermia has proven to be effective in cancer phototherapy [44], and the tissue-specific targeting of cancer and tumors via multi-modal HEVNPs can enhance the accuracy of targeting and efficacy during treatment.

Example 2: Heavy-Metal Nanocluster-Enhanced Viral Nanocapsids for Mucosal Delivery Problem: Hepatitis E nanoparticles (HEVNP) are capable of encapsulating therapeutics including nucleic acid, protein, and inorganic material. To enhance the tissue-specific targeting capabilities of HEVNP, both genetic and chemical modifications methodologies have been exploited by our lab in previous years (see recent publication: DOI: 10.3791/57020). Our goal is to deliver therapeutics to specific regions along the GI-tract in a controlled manner. Our previous knowledge indicates that the HEVNPs lose their icosahedral integrity, and therefore overall stability at higher pH values (+8), and therefore, may not be as effective for delivery to the distal regions of the colon (with pH ranging between 5-8.5). Our solution to this limitation was to utilize the heavy-metals, such as gold nanoclusters and use their resonance and magnetic characterizations to form a geometrical shield around and above the 5-fold axis of HEVNP (see details below). In our 2017 publication (Stark et al. 2017), we used advanced cryo-electron microscopy and single particle analysis techniques to characterize the location of the gold nanoclusters (AuNC) with a 6 carbon long spacer arm, bound to residue #N573C on the protrusion domain.

Solution: In our recent study, we discovered that AuNC-clusterization around and above the 5-fold icosahedral axis of HEVNP enhances its stability to resist to high pH degradation. Our goal is to expand HEVNP's capability as a nanodelivery platform to reach various gastro-intestinal regions with dynamic acidic conditions, for effective mucosal delivery of encapsulated drug via enhanced targeting and particle tracking modalities. Our previous establishments of IP's (including our recent publications) have been focused entirely on engineering the loops of our P-domain. This current disclosure of enhanced HEVNP is based on our functionalization in anchoring the gold-nanoclusters that would utilize the interplays of the M-S domains, as well as the lateral interface between the dimeric building blocks, based on the vertical imposition of pentameric nanoclusters on top of each five interconnected S-domains that would maintain the HEVNP capsid at the extended range of proton concentrations. Such rationalization has been evidenced with concept-proof in the enhanced structural integrity in a manuscript invited to be published in a special issue of nanomedicine.

Summary: Enhanced HEVNP Stability Via AuNC to Resist High pH Degradation (1) Geometrical constraint in AuNC conjugation by designated anchor/site: Conjugation of AuNC to the surface of HEVNP to achieve a cluster of AuNC over the 5-fold interface. Extendable spacer allows for necessary flexibility for the AuNC to form a cluster of clusters around the 5-fold axis. The doughnut-like geometrical distribution of the AuNC clusters around the 5-fold to protect key intermolecular interactions to enhance HEVNP stability at protonated state. Cryo-EM analysis indicates that the AuNC are horizontally (normal to 5-fold axis) flexible in the range of 2-3 nm and about 2 nm vertically.

(2) Geometrical shielding to protect key intermolecular interactions TYR288 and ASN200 at the 5-fold interface via AuNC clusterization: HEVNP assembly & disassembly: interplays of the M-S domains. The shell (S) and middle (M) domains are HEVNP are critical in assembly of fully functional HEVNPs. The dimeric building blocks of HEVNP form pentamers (pentamer of dimers: decamer). The decamers are stabilized by two key intermolecular interactions at the 5-fold interface: TYR288 and ASN200. The decamers are further stabilized into fully functional HEVNPs by formation of calcium bridges at the 3-fold icosahedral axis of HEVNP. Extendable spacer arm to provide stability for AuNC clusterization around the 5-fold axis; ranging between 5-12 units, covering three additional conjugation regions, in addition to previously established P domain residues: 483-490, 530-535, 554-561, 573-577, 582-593, and 601-613. Using radial distance as a reference point; the previously claimed residues are all +116 Angstroms above the center of HEVNP. Here we utilize 3 additional radially separated residues: 96 Angstroms; residue group 1: Residues 342-344; 106 Angstroms: residue group 2: Residues 402-408; 114 Angstroms: residue group 3: Residues 521-526

(3) Residues 402-408 on the middle domain of HENVP for cysteine mutation and chemical activation via thiol-exchange conjugation. Average distance away from the 5-fold axis ~32 Angstroms.

(4) Residues 342-344 on the middle domain of HENVP for cysteine mutation and chemical activation via thiol-exchange conjugation. Average distance away from the 5-fold axis ~26 Angstroms.

(5) Residues 521-526 on the middle domain of HENVP for cysteine mutation and chemical activation via thiol-exchange conjugation. Average distance away from the 5-fold axis ~41 Angstroms. *Reference to our previous work: distance between N573C to the 5-fold is about 35 Angstroms.

(6) Enhanced modularity of HEVNP additional anchor sites. Our previous establishment was focused entirely on the engineered loops on the protrusion domain. Here we expand the range of residues for the first time to the middle domain (residues: 402-408, 342-344, and an additional on protrusion domain, residues: 521-526). Our preliminary results and manuscripts in preparation suggest that these additional sites may be suitable for AuNC conjugation with extendable spacer length. Conjugation of AuNC to middle domain can enhance the stability of HEVNP to resist high pH degradation in a similar manner as we have shown with concept-proof in the enhanced structural integrity in a manuscript invited to be published in a special issue of nanomedicine. Although the specific interactions of the AuNC and 5-fold residues are not fully understood, the gained enhanced stability of the viral capsid allows for multi-modal surface modulation; conjugation of AuNC with spacer arm ranging between 5-12 units to the residue groups 1, 2 and 3, and utilize the previously established sites for additional modifications, such as targeting peptide conjugation. The resonance provided by the AuNC are excitable with photoacoustics which can be beneficial in imaging-guided hyperthermia, as well as particle tracking for both in vitro and in vivo studies.

Optimized Cation Concentrations for Efficient Encapsulation of Nucleic Acid

In order to encapsulate nucleic acid, the plasmid DNA for example, first needs to be condensed. This can be achieved using cations such as magnesium or manganese. While the usage of these positively charged elements facilitates DNA condensation, they could cause problems during particle reassembly by interfering with calcium bridges at the 3-fold. We have preliminary data suggesting that at optimized concentrations and timing of adding and removing calcium and magnesium, respectively, high efficiency in DNA encapsulation can be achieved. We have electron microscopy evidence that shows the formation of decamers, but not full HEVNP; we design the matrices to allow the contribution of the cation, e.g., $Mg^{2+}/Mn^{2+}$, in their interplays with the $Ca^{2+}$ ions over the HEVNP assembly. Therefore, the on-going parametric optimization will further detail the advanced conditions for efficiency-enhanced DNA encapsulation in a controlled manner.

Methodology for high efficiency plasmid DNA encapsulation using optimized cationic concentrations. We will encapsulate the DNA into HEVNPs with different parameters including the proton conc. at pH 4 to pH8; DNA condensing reagent using $Mg^{2+}/Mn^{2+}$ at 2 mM to 100 mM; HEVNP reassembly reagent using $Ca^{2+}$ at 2 mM to 50 mM. The kinetic factors of the DNA encapsulation will be analyzed by varying the total concentration of the mixture of HEVNPs and DNAs. The DNA encapsulation efficiency is analyzed by differential centrifugal sedimentation (DCS) after DNA encapsulation process. The DNA has been encapsulated will be measured and analyzed after HEVNP disassembly by the presence of DTT (1 mM-20 mM) and EGTA/EDTA (1 mM-10 mM).

Example 3: Gold Nanocluster Conjugation at Additional Sites on HEVNP

Introduction

The hepatitis E viral nanoparticles (HEVNP) is composed of 60 monomeric subunits, each composed of 3 domains: from N-terminus to C-terminus, Shell (S) residues 118-317, Middle (M) residues 318-451, Protruding (P) residues 452-606. The surface exposed P domain is comprised of multiple loops that can be (and have been) used for chemical and/or genetic insertion of peptides (such as targeting molecules or immunogenic peptides). We have designed additional conjugation sites on the M domain, for the first time. This enhanced multi-modal modularity on the P domain (residues: 493-498, 510-514, 520-525, 529-536, and 570-579) and M domain (residues: 342-344, and 402-408) enables the HEVNP platform to be used in a broader spectrum of applications (see FIG. 17). These applications can include chemotherapy, gene therapy, immunotherapy, radiotherapy (PET and SPET), magnetic hyperthermia (MM and MRI-guided treatment), phototherapy, photothermal ablation and optimal imaging, ultrasound imaging, vaccination, particle tracking and tissue distribution studies. Additionally, conjugation of gold nanoclusters has shown to enhance HEVNP's overall stability against pH or enzyme degradation. conjugation of gold nanoclusters and a linker arm (Au102-C6 (also written as AuNC)) to the position N573C on HEVNP's P domain—using chemical conjugation methods—illustrated that the AuNC tend to form clusters around the 5-fold axis of HEVNP. (Stark et al. 2017 SciRep). Baikoghli et al. 2018 illustrated that the HEVNP conjugated with Au102-C6 increases HEVNP's tolerance to avoid degradation at high pH values (>pH8). This enablement of the HEVNP construct broadens the applications of the nanoplatform to expand its range of treatment from tumor targeting to treatment of metabolic diseases, such as diabetes. The enhanced stability of the AuNC functionalized HEVNP extends its retention time to pass through the stomach and reach the portal vein, so that the release of drug, such as insulin can be achieved both intragastrical through oral delivery and also accumulate in the liver. The utility of cryo-EM tomography reconstruction methods unveils the unique encapsulation and packing of insulin detemir inside HEVNP (see FIG. 18).

Functionalization of the M Domain

Functionalities of the M domain is achieved through chemical engineering of site-specific amino acids into cysteines, which allow for thiol-based conjugation. Such engineered cysteine residues on the M domain of HEVNP provides an enhanced modular ability to the nanoparticles, by providing multiple anchoring sites on the surface. This is achieved by the geometrical configuration of HEVNP. As an example, and as shown in the conjugation of gold nanoclusters via a linker arm at position N573C on the P domain of HEVNP resulted in co-localization of gold nanoclusters (AKA superclusters), which in turn provide enhances stability to HEVNP (Stark et al. 2017, Baikoghli et al. 2018). Conjugation of these gold nanoclusters to M domain residues (342-344, and 402-408) is unprecedented and provides a more geometrically favorable clusterization, using an extendable linker arm. Linker arms made up of a carbon chain can be as long as 6-14 atoms. The modular nature of gold nanocluster can be utilized to optimize the highest stability of gold nanocluster co-localization. The geometrical constraint provided by the N573C conjugation site on the P domain as previously described, revealed by cryo-electron microscopy single particle analysis, showed an average distance of 35 Å away from the N573C site towards the 5-fold icosahedral axis of HEVNP at an angle of 27.5°. The M domain sites, residues in the range of 342-344 are on average 26 Å away from the center of the 5-fold icosahedral axis at an angle of 7.5°. The M domain sites, residues in the range of 402-408 are on average 32 Å away from the center of the 5-fold icosahedral axis at an angle of 9.5° (see FIG. 19).

Dual-Domain Peptide Conjugation

The epitopes on M domain (342-344 and 402-408) and P domain (493-498, 510-514, 520-525, 529-536, and 570-579) provide multiple anchoring points in optimal proximity for the insertion of two disparate ligands. For example, conjugation two disparate peptides onto the M domain and P domain using either chemical or genetic insertion can be utilized to form quaternary epitopes, formed from the two peptides. This structure-guided design is driven by the geometrical configuration of the dual-domain peptide insertion. As such, M domain functionalization enables the P domain to be "free" for additional functionalization. Dual-domain conjugation method enables HEVNP P domain to be used for targeting while M domain can carry specific therapeutic peptides or inorganic material for purposes of imaging-guided nanotheranostics. The epitopes on M domain (342-344 and 402-408) and P domain (493-498, 510-514, 520-525, 529-536, and 570-579) provide two anchoring points in optimal proximity for the insertion of two disparate ligands. Method of conjugation can be chemical and/or through genetic engineering. For example, the distance between site #1 (342C|M domain) and site #2 (573C|P domain) is measured 26.90 Å. The distance from 342C and 573C to the center of the 5-fold is 38.90 Å and 41.40 Å, respectively. The dual-insertion based on M domain only, or M domain and P domain combination is utilized to form conformational epitopes. As such, quaternary epitope formation based on two disparate insertions can be achieved through genetic and/or chemical conjugations (see FIGS. 20 and 21).

Additional P Domain Functionalization Sites

The P domain residues include residues 493-498, 510-514, 520-525, 529-536, and 570-579 for enhanced multi-domain functionalization. In addition to the 573C, the additional P domain residues can help enhance the resonance of the conjugated AuNC (as described above). The geometrical constraints of the HEVNP surface structure forces AuNC to form a cluster-of-clusters. The distance between the gold atoms allows for transfer of electrical signal across and around the cluster. In fact, using high-resolution cryo-EM (one of the top machines in the world—CryoARM 300 Cold-FEG Electron Microscope from JEOL)—we obtained electron microscope micrographs that indicate HEVNP binding to AuNC. The P domain sites can similarly be used for AuNC conjugation to the HEVNP. Since most of the sites are located near the periphery of HEVNP P domain dimers, the apical loops of the P domain are enabled to conjugate other functional peptides and/or targeting/tracking molecules (see FIG. 22).

Moreover, the insertion of AuNC at the conjugation sites on HEVNP enhances HEVNP's stability against degradation under harsh conditions, including pH and temperature (Baikoghli et al. 2018). Upon surface modulation with AuNC, the HEVNP withstands higher temperatures to avoid degradation. This has major implications for functionality of the nanoplatform, as well as implications of storage and delivery. Such enablement of the nanoplatform is a unique discovery towards enhanced stability of the HEVNP (see FIG. 23).

In addition, since the P domain residues are mainly on the periphery of HEVNP, functionalization with beta-paired anchors tag/catcher can increase the modular capacity of the nanoplatform. In particular, residues 570-579 are optimal for bp-tag insertion. The bp-catcher can be conjugated to larger proteins, such as insulin (for delivery and treatment of metabolic diseases, such as diabetes), which can then be covalently bound to the bp-tag on the surface of HEVNP. The linear structure of the bp-tag is optimal for surface functionalization of HEVNP since the conjugated structure does not interfere with HEVNP capsid formation (see FIG. 24).

Applications
Broadened Application Enablement

The utility of multi-domain functionalization (of M and P domains) towards enablement of HEVNP's functionality as a nanocarrier platform has applications in multiple disciplines including but not limited to chemotherapy; gene therapy; immunotherapy; radiotherapy, PET, and SPECT; magnetic Hyperthermia; MRI (and MM-guided treatment); phototherapy; X-ray CT/PAT; photothermal ablation and optical imaging; ultrasound imaging; vaccination; particle tracking and tissue distribution studies; and treatment of metabolic diseases.

Enhanced Stability

Conjugation of gold nanoclusters has been shown to enhance HEVNP's overall stability. For example, conjugation of gold nanoclusters and a linker arm (Au102-C6 (also written as AuNC)) to the position N573C on HEVNP's P domain—using chemical conjugation methods—illustrated that the AuNC tend to form clusters around the 5-fold axis of HEVNP (Stark et al. 2017 SciRep). In addition, Baikoghli et al. 2018 showed that the HEVNP conjugated with Au102-C6 increases HEVNP's tolerance to avoid degradation at high pH values (>pH8).

Enhanced Capacity of HEVNP to Deliver Drugs Under Harsh Physiological Conditions Enhanced capacity of HEVNP to deliver drugs under harsh physiological conditions includes applications in, for example, treatment of metabolic diseases; delivery of proteins (such as insulin for treatment of diabetes) to distal parts of the colon where the pH is generally high (ranging between pH 6.5-pH 9): encapsulation of insulin in HEVNP and increases stability of the nanocapsid provided by the resonance of AuNC; cryo-electron tomography methods were used to characterize the 3D structure of insulin-encapsulated HEVNP (see FIG. 18); functionalized HEVNP surface (either P domain (residues: (493-498, 510-514, 520-525, 529-536, 570-579) or the M domain (342-344, and 402-408)) can be utilized to guide the insulin encapsulated HEVNP to the proper tissue; and distribution of HEVNP can be monitored by heavy metals (such as AuNC) through MRI or TEM.

Functionalization of M Domain Residues
Multi-Domain Modularity Via Enablement of M Domain Conjugation Engineered Cysteine residues on the M domain of Hepatitis E viral nanoparticles (HEVNP) provides an enhanced modular ability to the nanoparticles, by providing multiple anchoring sites on the surface of HEVNP. Site-specific thiol-based conjugation of peptides and/or inorganic material, such as gold nanoclusters, is easily achieved at the surface-exposed residues of the M domain, falling within residues 342-344 (blue), and 402-408 (red) (see FIG. 19).

Geometrical Configuration of HEVNP AuNC

As shown in the conjugation of gold nanoclusters via a linker arm at position N573C on the P domain of HEVNP resulted in co-localization of gold nanoclusters (AKA superclusters), which in turn provide enhances stability to HEVNP (Stark et al. 2017, Baikoghli et al. 2018) (see FIG. 22). Conjugation of these gold nanoclusters to M domain residues (342-344, and 402-408) is unprecedented and provides a more geometrically favorable clusterization, using an extendable linker arm. Linker arms made up of a carbon chain can be as long as 6-14 atoms. The modular nature of gold nanocluster can be utilized to optimize the highest stability of gold nanocluster co-localization. The geometrical constraint provided by the N573C conjugation site on the P domain as previously described in (Stark et al. 2017, Baikoghli et al. 2018), revealed by cryo-electron microscopy single particle analysis, showed an average distance of 35 Å away from the N573C site towards the 5-fold icosahedral axis of HEVNP at an angle of 27.5°. The M domain sites, residues in the range of 342-344 are on average 26 Å away from the center of the 5-fold icosahedral axis at an angle of 7.5°. The M domain sites, residues in the range of 402-408 are on average 32 Å away from the center of the 5-fold icosahedral axis at an angle of 9.5°.

Multi-Domain Functionalization Using M and P Domains

M domain functionalization enables the P domain to be "free" for additional functionalization. Cysteine mutations on M domain residues 342-344 and 402-408 are utilized for conjugation of nanocluster inorganic material, such as gold nanoclusters and can be conjugated to small peptide used for cancer treatment, metabolic disease treatment, and/or treatment of metabolic diseases. Such dual-domain conjugation method enables HEVNP P domain to be used for targeting while M domain can carry specific therapeutic peptides or inorganic material for purposes of imaging-guided nanotheranostics.

Dual-Domain Peptide Conjugation

The epitopes on M domain (342-344 and 402-408) and P domain (493-498, 510-514, 520-525, 529-536, and 570-579) provide two anchoring points in optimal proximity for the insertion of two disparate ligands. Method of conjugation can be chemical and/or through genetic engineering. For example, an immunogenic peptide can be inserted to form a quaternary epitope: insertion of variable domain of Chlamydia immunogenic loops (e.g., epitopes from variable domain 2 at position 342C on the M domain and/or epitopes from variable domain 3 at position 573C on the P domain).

The two separately inserted epitopes are in perfect proximity to form a chimeric quaternary epitope.

Geometrical Configuration of the Dual-Domain Insertion

Distance between site #1 (342C|M domain) and site #2 (573C|P domain) (see FIGS. 20 and 21). Distance between farthest atoms of 342 and 573 is measured 26.90 Å. Distance of selected sites to the center of the 5-fold axis: 342C to the center of 5-Fold: 38.90 Å; 573C to the center of 5-Fold: 41.49 Å.

Functionalization of P Domain Residues

New Conjugation Sites on P Domain

P domain residues (493-498, 510-514, 520-525, 529-536, 570-579) can be used for enhanced multi-domain functionalization. Notable features include: (1) Resonance of AuNC: The geometrical constraints of the HEVNP surface structure forces AuNC to form a cluster-of-clusters. The distance between the gold atoms allows for transfer of electrical signal across and around the cluster. Using high-resolution cryo-EM (one of the top machines in the world—CryoARM 300 Cold-FEG Electron Microscope from JEOL)—we obtained electron microscope micrographs that indicate HEVNP binding to AuNC (see FIG. 22). The P domain sites can similarly be used for AuNC conjugation to the HEVNP. Since most of the sites are located near the periphery of HEVNP P domain dimers (see FIG. 22). (2) High-resolution structure determination using cryo-EM: Utility of cryo-EM to resolve the high-resolution structure of HEVNP conjugated to AuNC. Contrast transfer function signal shows maximum resolution to reach 3.1 Å (see FIG. 22). Data collection using direct electron detector technology to capture 40 frames (each frame exposure at 1.5 seconds) with a total electron dose of 67.5 $e^-/Å^2$. Motion correction to enhance image resolution and reduction of stigmatism. Individual AuNC are finely resolved and HEVNP are clearly observed in the background. (3) Enhanced stability: the insertion of AuNC at the conjugation sites on HEVNP enhances HEVNP's stability against degradation under harsh conditions, including pH (discussed under 1.2.1) and temperature. Newly identified conjugation sites on HEVNP can facilitate AuNC and/or magnetic metals to increase the stability of HEVNP against temperature-driven degradation. TEM analysis illustrates the enhanced stability of HEVNP as a function of increased temperature (see FIG. 23).

Functionalized Beta-Paired Tag/Catcher Conjugation to the Surface Exposed P Domain Utilization of the residues on the periphery of HEVNP to insert (either genetically or by chemical methods) a bp-tag peptide, which is recognized by bp-catcher protein (see FIG. 24) offers these applications: functionalization of bp-catcher with proteins of interest; efficient and broadened range of conjugation towards treatment of metabolic diseases and targeting of tumor.

While the direct insertion (with or without extended linkers) of small peptides or metals (such as AuNC) directly onto the genetically modified HEV-VLP Cys sites provides a suitable nanoplatform, the usage of (beta-paired: BP) BP-Tag and BP-Catcher can allow for larger proteins (such as enzymes) to be conjugated to the surface of functionalized HEV-VLP. Such enablement broadens the scope of functionality of the HEV-VLP nanoparticles in areas such as vaccination, hydrogen formation, and multivalent activation of signaling. Phase I conjugation of the BP-tag or BP-catcher (depending on the application) onto the HEV-VLP can be achieved by S-S (thiol-based) conjugation using maleimide linker arms, while would provide a platform for phase II conjugation of larger proteins.

All patents, patent applications, and other publications, including GenBank Accession Numbers, cited in this application are incorporated by reference in the entirety for all purposes.

REFERENCES

1. Zhang, L., et al., Nanoparticles in medicine: therapeutic applications and developments. 247 Clinical pharmacology & therapeutics, 2008. 83(5): p. 761-769. 248
2. Zhao, L., et al., Nanoparticle vaccines. Vaccine, 2014. 32(3): p. 327-337. 249
3. Choi, K. Y., et al., Theranostic nanoplatforms for simultaneous cancer imaging and 250 therapy: current approaches and future perspectives. Nanoscale, 2012. 4(2): p. 330-342. 251
4. Yildiz, I., S. Shukla, and N. F. Steinmetz, Applications of viral nanoparticles in medicine. 252 Current opinion in biotechnology, 2011. 22(6): p. 901-908. 253
5. Roldão, A., et al., Virus-like particles in vaccine development. Expert review of vaccines, 254 2010. 9(10): p. 1149-1176. 255
6. Pinto, L. A., et al., Cellular immune responses to human papillomavirus (HPV)-16 L1 in 256 healthy volunteers immunized with recombinant HPV-16 L1 virus-like particles. The 257 Journal of infectious diseases, 2003. 188(2): p. 327-338. 258
7. Ma, Y., R. J. Nolte, and J. J. Cornelissen, Virus-based nanocarriers for drug delivery. 259
Advanced drug delivery reviews, 2012. 64(9): p. 811-825. 260
8. Molino, N. M. and S.-W. Wang, Caged protein nanoparticles for drug delivery. Current 261 opinion in biotechnology, 2014. 28: p. 75-82. 262
9. Garcea, R. L. and L. Gissmann, Virus-like particles as vaccines and vessels for the delivery 263 of small molecules. Current opinion in biotechnology, 2004. 15(6): p. 513-517. 264
10. Schoonen, L. and J. C. van Hest, Functionalization of protein-based nanocages for drug 265 delivery applications. Nanoscale, 2014. 6(13): p. 7124-7141. 266
11. Chen, C.-C., et al., Chemically activatable viral capsid functionalized for cancer targeting. 267 Nanomedicine, 2016. 11(4): p. 377-390. 268
12. Chen, C.-C., et al., Hepatitis E Virus Nanoparticle Encapsulating Nano-Theranostic 269 Reagent as Modularized Capsule. 270
13. Stark, M. and R. H. Cheng, Surface modulatable nanocapsids for targeting and tracking 271 toward nanotheranostic delivery. Pharmaceutical patent analyst, 2016. 5(5): p. 307-317. 272
14. Takamura, S., et al., DNA vaccine-encapsulated virus-like particles derived from an orally 273 transmissible virus stimulate mucosal and systemic immune responses by oral 274 administration. Gene therapy, 2004. 11(7): p. 628. 275
15. Jariyapong, P., et al., Chimeric hepatitis E virus-like particle as a carrier for oral-delivery. 276 Vaccine, 2013. 31(2): p. 417-424. 277
16. Holla, P., et al., Toward Mucosal DNA Delivery: Structural Modularity in Vaccine Platform 278 Design, in Micro and Nanotechnology in Vaccine Development. 2017, Elsevier. p. 303-279 326. 280
17. Chen, C. C., M. A. Baikoghli, and R. H. Cheng, Tissue targeted nanocapsids for oral insulin 281 delivery via drink. 2018, Future Science. 282

18. Xing, L., et al., Recombinant hepatitis E capsid protein self-assembles into a dual-domain 283 T=1 particle presenting native virus epitopes. Virology, 1999. 265(1): p. 35-45. 284
19. Xing, L., et al., Structure of hepatitis E virion-sized particle reveals an RNA-dependent 285 viral assembly pathway. Journal of Biological Chemistry, 2010. 285(43): p. 33175-33183. 286
20. Xing, L., et al., Spatial configuration of hepatitis E virus antigenic domain. Journal of 287 virology, 2011. 85(2): p. 1117-1124. 288
21. Li, T.-C., et al., Essential elements of the capsid protein for self-assembly into empty 289 virus-like particles of hepatitis E virus. Journal of virology, 2005. 79(20): p. 12999-13006. 290
22. Mori, Y. and Y. Matsuura, Structure of hepatitis E viral particle. Virus research, 2011. 291 161(1): p. 59-64. 292
23. Yamashita, T., et al., Biological and immunological characteristics of hepatitis E virus-like 293 particles based on the crystal structure. Proceedings of the National Academy of 294 Sciences, 2009. 106(31): p. 12986-12991. 295
24. Xiao, W., et al., Discovery and characterization of a high-affinity and high-specificity 296 peptide ligand LXY30 for in vivo targeting of a3 integrin-expressing human tumors. 297 EJNMMI research, 2016. 6(1): p. 18. 298
25. Stark, M. C., et al., Structural characterization of site-modified nanocapsid with 299 monodispersed gold clusters. Scientific reports, 2017. 7(1): p. 17048. 300
26. Koivisto, J., et al., Acid-Base Properties and Surface Charge Distribution of the Water-301 Soluble Au102 (p MBA) 44 Nanocluster. The Journal of Physical Chemistry C, 2016. 302 120(18): p. 10041-10050. 303
27. Lahtinen, T., et al., Template-Free Supracolloidal Self-Assembly of Atomically Precise 304 Gold Nanoclusters: From 2D Colloidal Crystals to Spherical Capsids. Angewandte Chemie 305 International Edition, 2016. 55(52): p. 16035-16038. 306
28. Hulkko, E., et al., Electronic and Vibrational Signatures of the Au102 (p-MBA) 44 Cluster. 307 Journal of the American Chemical Society, 2011. 133(11): p. 3752-3755. 308
29. Jadzinsky, P. D., et al., Structure of a thiol monolayer-protected gold nanoparticle at 1.1 Å 309 resolution. Science, 2007. 318(5849): p. 430-433. 310
30. Salorinne, K., et al., Conformation and dynamics of the ligand shell of a water-soluble Au 311 102 nanoparticle. Nature communications, 2016. 7: p. 10401. 312
31. Guo, F. and W. Jiang, Single particle cryo-electron microscopy and 3-D reconstruction of 313 viruses, in Electron Microscopy. 2014, Springer. p. 401-443. 314
32. Baker, T. S. and R. H. Cheng, A model-based approach for determining orientations of 315 biological macromolecules imaged by cryoelectron microscopy. Journal of structural 316 biology, 1996. 116(1): p. 120-130. 317
33. Acar, E., et al., Multiresolution MAPEM Method for 3D Reconstruction of Symmetrical 318 Particles with Electron Microscopy, in EMBEC & NBC 2017. 2017, Springer. p. 141-144. 319
34. Ludtke, S. J., P. R. Baldwin, and W. Chiu, EMAN: semiautomated software for high-320 resolution single-particle reconstructions. Journal of structural biology, 1999. 128(1): p. 321 82-97. 322
35. Li, T.-C., et al., Expression and self-assembly of empty virus-like particles of hepatitis E 323 virus. Journal of virology, 1997. 71(10): p. 7207-7213. 324
36. Schindelin, J., et al., Fiji: an open-source platform for biological-image analysis. Nature 325 methods, 2012. 9(7): p. 676. 326
37. Ruthardt, N., D. C. Lamb, and C. Bräuchle, Single-particle tracking as a quantitative 327 microscopy-based approach to unravel cell entry mechanisms of viruses and 328 pharmaceutical nanoparticles. Molecular therapy, 2011. 19(7): p. 1199-1211. 329
38. Salorinne, K., et al., Solvation chemistry of water-soluble thiol-protected gold 330 nanocluster Au 102 from DOSY NMR spectroscopy and DFT calculations. Nanoscale, 331 2014. 6(14): p. 7823-7826. 332
39. Paavolainen, L., et al., Compensation of missing wedge effects with sequential statistical 333 reconstruction in electron tomography. PloS one, 2014. 9(10): p. e108978. 334
40. Soonsawad, P., et al., Structural evidence of glycoprotein assembly in cellular membrane 335 compartments prior to Alphavirus budding. Journal of virology, 2010. 84(21): p. 11145-336 11151. 337
41. Eustis, S. and M. A. El-Sayed, Why gold nanoparticles are more precious than pretty gold: 338 noble metal surface plasmon resonance and its enhancement of the radiative and 339 nonradiative properties of nanocrystals of different shapes. Chemical society reviews, 340 2006. 35(3): p. 209-217. 341
42. Malola, S., et al., Birth of the localized surface plasmon resonance in monolayer-342 protected gold nanoclusters. Acs Nano, 2013. 7(11): p. 10263-10270. 343
43. Ghosh, S. K. and T. Pal, Interparticle coupling effect on the surface plasmon resonance of 344 gold nanoparticles: from theory to applications. Chemical reviews, 2007. 107(11): p. 345 4797-4862. 346
44. Terentyuk, G. S., et al., Laser-induced tissue hyperthermia mediated by gold 347 nanoparticles: toward cancer phototherapy. Journal of biomedical optics, 2009. 14(2): p. 348 021016.

What is claimed is:

1. A composition comprising:

(i) a modified capsid protein comprising a portion of hepatitis E virus (HEV) open Reading Frame 2 (ORF2) protein, wherein at least one amino acid in the 342-344, 402-408, 510-514, 493-498, 570-579, 529-536, or 520-525 segment of the HEV ORF2 protein amino acid sequence set forth in SEQ ID NO:1 or the corresponding segment of SEQ ID NO:2, 3, 4, 5, or 6 is replaced with a cysteine, which is conjugated with a nanocluster of an element selected from Groups 3 through 18 having an atomic number greater than 20; and (ii) a bioactive agent encapsulated in an HEV virus-like particle (VLP) formed by the modified capsid protein, wherein the bioactive agent is (1) a polynucleotide sequence encoding an insulin, proinsulin, or pre-proinsulin polypeptide or (2) an insulin, proinsulin, or pre-proinsulin polypeptide.

2. The composition of claim 1, wherein the element is gold.

3. The composition of claim 1, wherein amino acid residue 342 and/or 573 of the HEV ORF2 protein amino acid sequence set forth in SEQ ID NO:1 or the corresponding residue of SEQ ID NO:2, 3, 4, 5, or 6 is replaced with a cysteine.

4. The composition of claim 2, wherein the cysteine is chemically derivatized and conjugated with the gold nanocluster via a linker.

5. The composition of claim 1, wherein the nanocluster is about 2-3 nm horizontally and about 2 nm vertically from the cysteine.

6. The composition of claim 1, wherein the nanocluster is about 1.5-3 nm in diameter.

7. The composition of claim 2, wherein the cysteine is derivatized with a 6-carbon spacer.

8. The composition of claim 7, wherein the 6-carbon spacer is pMBA44.

9. The composition of claim 8, wherein the cysteine is conjugated with the gold nanocluster via maleimide linker.

10. The composition of claim 3, wherein the cysteine is derivatized with a 6-carbon spacer pMBA44 and conjugated with the gold nanocluster via maleimide linker.

11. The composition of claim 1, further comprising a pharmaceutically acceptable excipient.

12. The composition of claim 1, which is formulated for oral administration.

13. A method of targeted delivery of a bioactive agent comprising contacting a liver cell with the composition of claim 1.

14. The method of claim 13, wherein the liver cell is within a patient's body, and wherein the contacting step comprises administration of the composition of claim 9 to the patient.

15. The method of claim 13, wherein the administration is oral administration.

16. The method of claim 14, wherein the modified capsid protein is derivatized with pMBA44 and conjugated to a gold nanocluster via maleimide linker.

17. The method of claim 13, wherein the bioactive agent is a polynucleotide sequence encoding an insulin, proinsulin, or pre-proinsulin.

18. The method of claim 13, wherein the bioactive agent is an insulin polypeptide.

19. The method of claim 13, wherein the patient has been diagnosed with diabetes.

* * * * *

SEQUENCE LISTING

```
<160> NUMBER OF SEQ ID NOS: 15

<210> SEQ ID NO 1
<211> LENGTH: 660
<212> TYPE: PRT
<213> ORGANISM: Hepatitis E virus

<400> SEQUENCE: 1

Met Arg Pro Arg Pro Ile Leu Leu Leu Leu Met Phe Leu Pro Met
1               5                   10                  15
```

-continued

Leu Pro Ala Pro Pro Gly Gln Pro Ser Gly Arg Arg Gly Arg
            20              25              30

Arg Ser Gly Gly Ser Gly Gly Phe Trp Gly Asp Arg Ala Asp Ser
        35              40              45

Gln Pro Phe Ala Ile Pro Tyr Ile His Pro Thr Asn Pro Phe Ala Pro
    50              55              60

Asp Val Thr Ala Ala Gly Ala Gly Pro Arg Val Arg Gln Pro Ala
65          70              75              80

Arg Pro Leu Gly Ser Ala Trp Arg Asp Gln Ala Gln Pro Ala Ala
            85              90              95

Ala Ser Arg Arg Arg Pro Thr Thr Ala Gly Ala Ala Pro Leu Thr Ala
        100             105             110

Val Ala Pro Ala His Asp Thr Pro Pro Val Pro Asp Val Asp Ser Arg
    115             120             125

Gly Ala Ile Leu Arg Arg Gln Tyr Asn Leu Ser Thr Ser Pro Leu Thr
    130             135             140

Ser Ser Val Ala Thr Gly Thr Asn Leu Val Leu Tyr Ala Ala Pro Leu
145             150             155             160

Ser Pro Leu Leu Pro Leu Gln Asp Gly Thr Asn Thr His Ile Met Ala
            165             170             175

Thr Glu Ala Ser Asn Tyr Ala Gln Tyr Arg Val Val Arg Ala Thr Ile
        180             185             190

Arg Tyr Arg Pro Leu Val Pro Asn Ala Val Gly Gly Tyr Ala Ile Ser
        195             200             205

Ile Ser Phe Trp Pro Gln Thr Thr Thr Pro Thr Ser Val Asp Met
210             215             220

Asn Ser Ile Thr Ser Thr Asp Val Arg Ile Leu Val Gln Pro Gly Ile
225             230             235             240

Ala Ser Glu His Val Ile Pro Ser Glu Arg Leu His Tyr Arg Asn Gln
            245             250             255

Gly Trp Arg Ser Val Glu Thr Ser Gly Val Ala Glu Glu Ala Thr
        260             265             270

Ser Gly Leu Val Met Leu Cys Ile His Gly Ser Leu Val Asn Ser Tyr
        275             280             285

Thr Asn Thr Pro Tyr Thr Gly Ala Leu Gly Leu Leu Asp Phe Ala Leu
    290             295             300

Glu Leu Glu Phe Arg Asn Leu Thr Pro Gly Asn Thr Asn Thr Arg Val
305             310             315             320

Ser Arg Tyr Ser Ser Thr Ala Arg His Arg Leu Arg Arg Gly Ala Asp
        325             330             335

Gly Thr Ala Glu Leu Thr Thr Thr Ala Ala Thr Arg Phe Met Lys Asp
        340             345             350

Leu Tyr Phe Thr Ser Thr Asn Gly Val Gly Glu Ile Gly Arg Gly Ile
        355             360             365

Ala Leu Thr Leu Phe Asn Leu Ala Asp Thr Leu Leu Gly Gly Leu Pro
    370             375             380

Thr Glu Leu Ile Ser Ser Ala Gly Gly Gln Leu Phe Tyr Ser Arg Pro
385             390             395             400

Val Val Ser Ala Asn Gly Glu Pro Thr Val Lys Leu Tyr Thr Ser Val
            405             410             415

Glu Asn Ala Gln Gln Asp Lys Gly Ile Ala Ile Pro His Asp Ile Asp
        420             425             430

Leu Gly Glu Ser Arg Val Val Ile Gln Asp Tyr Asp Asn Gln His Glu

```
                  435                 440                 445
Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
                500                 505                 510

Ser Leu Asp Trp Thr Lys Val Thr Leu Asp Gly Arg Pro Leu Ser Thr
                515                 520                 525

Thr Gln Gln Tyr Ser Lys Thr Phe Phe Val Leu Pro Leu Arg Gly Lys
530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
                580                 585                 590

Val Ser Ile Ser Ala Val Ala Val Leu Ala Pro His Ser Ala Leu Ala
                595                 600                 605

Leu Leu Glu Asp Thr Met Asp Tyr Pro Ala Arg Ala His Thr Phe Asp
610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
        660

<210> SEQ ID NO 2
<211> LENGTH: 660
<212> TYPE: PRT
<213> ORGANISM: Hepatitis E virus

<400> SEQUENCE: 2

Met Arg Pro Arg Ala Val Leu Leu Phe Phe Val Leu Leu Pro Met
1               5                   10                  15

Leu Pro Ala Pro Pro Ala Gly Gln Pro Ser Gly Arg Arg Gly Arg
                20                  25                  30

Arg Ser Gly Gly Ala Gly Gly Phe Trp Gly Asp Arg Val Asp Ser
                35                  40                  45

Gln Pro Phe Ala Leu Pro Tyr Ile His Pro Thr Asn Pro Phe Ala Ala
    50                  55                  60

Asp Val Val Ser Gln Ser Gly Ala Gly Ala Arg Pro Arg Gln Pro Pro
65                  70                  75                  80

Arg Pro Leu Gly Ser Ala Trp Arg Asp Gln Ser Gln Arg Pro Ser Ala
                85                  90                  95

Ala Pro Arg Arg Arg Ser Ala Pro Ala Gly Ala Ala Pro Leu Thr Ala
                100                 105                 110

Ile Ser Pro Ala Pro Asp Thr Ala Pro Val Pro Asp Val Asp Ser Arg
                115                 120                 125

Gly Ala Ile Leu Arg Arg Gln Tyr Asn Leu Ser Thr Ser Pro Leu Thr
            130                 135                 140
```

```
Ser Ser Val Ala Ser Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
            165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
            245                 250                 255

Gly Trp Arg Ser Val Glu Thr Thr Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
            290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
            325                 330                 335

Gly Thr Ala Glu Leu Thr Thr Thr Ala Ala Thr Arg Phe Met Lys Asp
            340                 345                 350

Leu His Phe Thr Gly Thr Asn Gly Val Gly Glu Val Gly Arg Gly Ile
            355                 360                 365

Ala Leu Thr Leu Phe Asn Leu Ala Asp Thr Leu Leu Gly Gly Leu Pro
            370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
            405                 410                 415

Glu Asn Ala Gln Gln Asp Lys Gly Ile Thr Ile Pro His Asp Ile Asp
            420                 425                 430

Leu Gly Asp Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
            485                 490                 495

Thr Val Thr Phe Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
            515                 520                 525

Ile Gln Gln Tyr Ser Lys Thr Phe Tyr Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Ala Gly
```

```
                        565                 570                 575

His Arg Val Ala Ile Ser Thr Tyr Thr Thr Ser Leu Gly Ala Gly Pro
                580                 585                 590

Thr Ser Ile Ser Ala Val Gly Val Leu Ala Pro His Ser Ala Leu Ala
                595                 600                 605

Val Leu Glu Asp Thr Thr Asp Tyr Pro Ala Arg Ala His Thr Phe Asp
                610                 615                 620

Asp Phe Cys Pro Glu Cys Arg Thr Leu Gly Leu Gln Gly Cys Ala Phe
625                 630                 635                 640

Gln Ser Thr Ile Ala Glu Leu Gln Arg Leu Lys Met Lys Val Gly Lys
                645                 650                 655

Thr Arg Glu Ser
            660

<210> SEQ ID NO 3
<211> LENGTH: 660
<212> TYPE: PRT
<213> ORGANISM: Hepatitis E virus

<400> SEQUENCE: 3

Met Arg Pro Arg Ala Val Leu Leu Leu Phe Phe Val Leu Leu Pro Met
1               5                   10                  15

Leu Pro Ala Pro Pro Ala Gly Gln Pro Ser Gly Arg Arg Gly Arg
                20                  25                  30

Arg Ser Gly Gly Thr Gly Gly Gly Phe Trp Gly Asp Arg Val Asp Ser
                35                  40                  45

Gln Pro Phe Ala Leu Pro Tyr Ile His Pro Thr Asn Pro Phe Ala Ser
                50                  55                  60

Asp Ile Pro Thr Ala Thr Gly Ala Gly Ala Arg Pro Arg Gln Pro Ala
65                  70                  75                  80

Arg Pro Leu Gly Ser Ala Trp Arg Asp Gln Ser Gln Arg Pro Ala Ala
                85                  90                  95

Pro Ala Arg Arg Arg Ser Ala Pro Ala Gly Ala Ser Pro Leu Thr Ala
                100                 105                 110

Val Ala Pro Ala Pro Asp Thr Ala Pro Val Pro Asp Val Asp Ser Arg
                115                 120                 125

Gly Ala Ile Leu Arg Arg Gln Tyr Asn Leu Ser Thr Ser Pro Leu Thr
                130                 135                 140

Ser Thr Ile Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Ile Ala
                165                 170                 175

Thr Glu Ala Ser Asn Tyr Ala Gln Tyr Arg Val Val Arg Ala Thr Ile
                180                 185                 190

Arg Tyr Arg Pro Leu Val Pro Asn Ala Val Gly Gly Tyr Ala Ile Ser
                195                 200                 205

Ile Ser Phe Trp Pro Gln Thr Thr Thr Pro Thr Ser Val Asp Met
                210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
                260                 265                 270
```

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
        290                 295                 300

Glu Leu Glu Phe Arg Asn Leu Thr Pro Gly Asn Thr Asn Thr Arg Val
305                 310                 315                 320

Ser Arg Tyr Ser Ser Ser Ala Arg His Lys Leu Cys Arg Gly Pro Asp
                325                 330                 335

Gly Thr Ala Glu Leu Thr Thr Thr Ala Thr Arg Phe Met Lys Asp
            340                 345                 350

Leu His Phe Thr Gly Thr Asn Gly Val Gly Glu Val Gly Arg Gly Ile
        355                 360                 365

Ala Leu Thr Leu Leu Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
    450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
                485                 490                 495

Thr Val Thr Phe Val Asn Val Ala Thr Gly Thr Gln Gly Val Ser Arg
            500                 505                 510

Ser Leu Asp Trp Ser Lys Val Thr Leu Asp Gly Arg Pro Leu Thr Thr
        515                 520                 525

Ile Gln Gln Tyr Ser Lys Thr Phe Phe Val Leu Pro Leu Arg Gly Lys
    530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Pro Gly
                565                 570                 575

His Arg Val Cys Ile Ser Thr Tyr Thr Thr Asn Leu Gly Ser Gly Pro
            580                 585                 590

Val Ser Ile Ser Ala Val Gly Val Leu Ala Pro His Ser Ala Leu Ala
        595                 600                 605

Ala Leu Glu Asp Thr Val Asp Tyr Pro Ala Arg Ala His Thr Phe Asp
    610                 615                 620

Asp Phe Cys Pro Glu Cys Arg Ala Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Gln Glu Tyr
            660

<210> SEQ ID NO 4
<211> LENGTH: 659
<212> TYPE: PRT

<213> ORGANISM: Hepatitis E virus

<400> SEQUENCE: 4

```
Met Arg Pro Arg Pro Leu Leu Leu Leu Phe Leu Leu Phe Leu Pro Met
1               5                   10                  15

Leu Pro Ala Pro Pro Thr Gly Gln Pro Ser Gly Arg Arg Arg Gly Arg
            20                  25                  30

Arg Ser Gly Gly Thr Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asp Val Ala Ala Ala Ser Gly Ser Gly Pro Arg Leu Arg Gln Pro Ala
65                  70                  75                  80

Arg Pro Leu Gly Ser Thr Trp Arg Asp Gln Ala Gln Arg Pro Ser Ala
            85                  90                  95

Ala Ser Arg Arg Arg Pro Ala Thr Ala Gly Ala Ala Leu Thr Ala
        100                 105                 110

Val Ala Pro Ala His Asp Thr Ser Pro Val Pro Asp Val Asp Ser Arg
            115                 120                 125

Gly Ala Ile Leu Arg Arg Gln Tyr Asn Leu Ser Thr Ser Pro Leu Thr
130                 135                 140

Ser Ser Val Ala Ser Gly Thr Asn Leu Val Leu Tyr Ala Ala Pro Leu
145                 150                 155                 160

Asn Pro Pro Leu Pro Leu Gln Asp Gly Thr Asn Thr His Ile Met Ala
            165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
            245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
            290                 295                 300

Glu Leu Glu Phe Arg Asn Leu Thr Thr Cys Asn Thr Asn Thr Arg Val
305                 310                 315                 320

Ser Arg Tyr Ser Ser Thr Ala Arg His Ser Arg Gly Ala Asp Gly
            325                 330                 335

Thr Ala Glu Leu Thr Thr Thr Ala Ala Thr Arg Phe Met Lys Asp Leu
            340                 345                 350

His Phe Thr Gly Leu Asn Gly Val Gly Glu Val Gly Arg Gly Ile Ala
            355                 360                 365

Leu Thr Leu Leu Asn Leu Ala Asp Thr Leu Leu Gly Gly Leu Pro Thr
            370                 375                 380

Glu Leu Ile Ser Ser Ala Gly Gly Gln Leu Phe Tyr Ser Arg Pro Val
385                 390                 395                 400
```

```
Val Ser Ala Asn Gly Glu Pro Thr Val Lys Leu Tyr Thr Ser Val Glu
                405                 410                 415

Asn Ala Gln Gln Asp Lys Gly Val Ala Ile Pro His Asp Ile Asp Leu
            420                 425                 430

Gly Asp Ser Arg Val Val Ile Gln Asp Tyr Asp Asn Gln His Glu Gln
        435                 440                 445

Asp Arg Pro Thr Pro Ser Pro Ala Pro Ser Arg Pro Phe Ser Val Leu
    450                 455                 460

Arg Ala Asn Asp Val Leu Trp Leu Ser Leu Thr Ala Ala Glu Tyr Asp
465                 470                 475                 480

Gln Ser Thr Tyr Gly Ser Ser Thr Gly Pro Val Tyr Ile Ser Asp Ser
                485                 490                 495

Val Thr Leu Val Asn Val Ala Thr Gly Ala Gln Ala Val Ala Arg Ser
                500                 505                 510

Leu Asp Trp Ser Lys Val Thr Leu Asp Gly Arg Pro Leu Pro Thr Val
            515                 520                 525

Glu Gln Tyr Ser Lys Thr Phe Phe Val Leu Pro Leu Arg Gly Lys Leu
        530                 535                 540

Ser Phe Trp Glu Ala Gly Thr Thr Lys Ala Gly Tyr Pro Tyr Asn Tyr
545                 550                 555                 560

Asn Thr Thr Ala Ser Asp Gln Ile Leu Ile Glu Asn Ala Ala Gly His
                565                 570                 575

Arg Val Ala Ile Ser Thr Tyr Thr Thr Arg Leu Gly Ala Gly Pro Val
                580                 585                 590

Ala Ile Ser Ala Ala Ala Val Leu Ala Pro Arg Ser Ala Leu Ala Leu
            595                 600                 605

Leu Glu Asp Thr Phe Asp Tyr Pro Gly Arg Ala His Thr Phe Asp Asp
        610                 615                 620

Phe Cys Pro Glu Cys Arg Ala Leu Gly Leu Gln Gly Cys Ala Phe Gln
625                 630                 635                 640

Ser Thr Val Ala Glu Leu Gln Arg Leu Lys Val Lys Val Gly Lys Thr
                645                 650                 655

Arg Glu Leu

<210> SEQ ID NO 5
<211> LENGTH: 674
<212> TYPE: PRT
<213> ORGANISM: Hepatitis E virus
<220> FEATURE:
<221> NAME/KEY: MOD_RES
<222> LOCATION: (368)..(368)
<223> OTHER INFORMATION: Any amino acid

<400> SEQUENCE: 5

Met Asn Asn Met Phe Leu Cys Phe Ala Cys Gly Tyr Ala Thr Met Arg
1               5                   10                  15

Pro Arg Ala Ile Leu Leu Leu Leu Val Val Leu Leu Pro Met Leu Pro
            20                  25                  30

Ala Pro Pro Ala Gly Gln Ser Ser Gly Arg Arg Gly Arg Arg Ser
        35                  40                  45

Gly Gly Ala Gly Ser Gly Phe Trp Gly Asp Arg Val Asp Ser Gln Pro
    50                  55                  60

Phe Ala Leu Pro Tyr Ile His Pro Thr Asn Pro Phe Ala Ser Asp Thr
65                  70                  75                  80

Ile Ala Ala Thr Gly Thr Gly Ala Arg Ser Arg Gln Ser Ala Arg Pro
                85                  90                  95
```

```
Leu Gly Ser Ala Trp Arg Asp Gln Thr Gln Arg Pro Pro Ala Ala Ser
            100                 105                 110

Arg Arg Arg Ser Thr Pro Thr Gly Ala Ser Pro Leu Thr Ala Val Ala
            115                 120                 125

Pro Ala Pro Asp Thr Arg Pro Val Pro Asp Val Asp Ser Arg Gly Ala
            130                 135                 140

Ile Leu Arg Arg Gln Tyr Asn Leu Ser Thr Ser Pro Leu Thr Ser Thr
145                 150                 155                 160

Ile Ala Ser Gly Thr Asn Leu Val Leu Tyr Ala Ala Pro Leu Ser Pro
                165                 170                 175

Leu Leu Pro Leu Gln Asp Gly Thr Asn Thr His Ile Met Ala Thr Glu
            180                 185                 190

Ala Ser Asn Tyr Ala Gln Tyr Arg Val Val Arg Ala Thr Ile Arg Tyr
            195                 200                 205

Arg Pro Leu Val Pro Asn Ala Val Gly Gly Tyr Ala Ile Ser Ile Ser
            210                 215                 220

Phe Trp Pro Gln Thr Thr Thr Pro Thr Ser Val Asp Met Asn Ser
225                 230                 235                 240

Ile Thr Ser Thr Asp Val Arg Ile Val Val Gln Pro Gly Leu Ala Ser
                245                 250                 255

Glu Leu Val Ile Pro Ser Glu Arg Leu His Tyr Arg Asn Gln Gly Trp
            260                 265                 270

Arg Ser Val Glu Thr Ser Gly Val Ala Glu Glu Ala Thr Ser Gly
            275                 280                 285

Leu Val Met Leu Cys Ile His Gly Ser Pro Val Asn Ser Tyr Thr Asn
            290                 295                 300

Thr Pro Tyr Thr Gly Ala Leu Gly Leu Leu Asp Phe Ala Leu Glu Leu
305                 310                 315                 320

Glu Phe Arg Asn Leu Thr Pro Gly Asn Thr Asn Thr Arg Val Ser Arg
                325                 330                 335

Tyr Ser Ser Thr Ala Arg His Arg Leu His Arg Gly Ala Asp Gly Thr
                340                 345                 350

Ala Glu Leu Thr Thr Thr Ala Ala Thr Arg Phe Met Lys Asp Leu Xaa
            355                 360                 365

Phe Thr Gly Ser Asn Gly Ile Gly Glu Val Gly Arg Gly Ile Ala Leu
            370                 375                 380

Thr Leu Phe Asn Leu Ala Asp Thr Leu Leu Gly Gly Leu Pro Thr Glu
385                 390                 395                 400

Leu Ile Ser Ser Ala Gly Gly Gln Leu Phe Tyr Ser Arg Pro Val Val
                405                 410                 415

Ser Ala Asn Gly Glu Pro Thr Val Lys Leu Tyr Thr Ser Val Glu Asn
            420                 425                 430

Ala Gln Gln Asp Lys Gly Ile Ala Ile Pro His Asp Ile Asp Leu Gly
            435                 440                 445

Asp Ser Arg Val Val Ile Gln Asp Tyr Asp Asn Gln His Glu Gln Asp
            450                 455                 460

Arg Pro Thr Pro Ser Pro Ala Pro Ser Arg Pro Phe Ser Val Leu Arg
465                 470                 475                 480

Val Asn Asp Val Leu Trp Leu Thr Met Thr Ala Ala Glu Tyr Asp Gln
                485                 490                 495

Thr Thr Tyr Gly Thr Ser Thr Asp Pro Val Tyr Val Ser Asp Thr Val
            500                 505                 510
```

```
Thr Phe Val Asn Val Ala Thr Gly Ala Gln Gly Val Ala Arg Ser Leu
            515                 520                 525

Asp Trp Ser Lys Val Thr Leu Asp Gly Arg Pro Leu Thr Thr Ile Gln
530                 535                 540

Arg His Ser Lys Asn Tyr Phe Val Leu Pro Leu Arg Gly Lys Leu Ser
545                 550                 555                 560

Phe Trp Glu Ala Gly Thr Thr Lys Ala Gly Tyr Pro Tyr Asn Tyr Asn
                565                 570                 575

Thr Thr Ala Ser Asp Gln Ile Leu Ile Glu Asn Ala Ala Gly His Arg
            580                 585                 590

Val Cys Ile Ser Thr Tyr Thr Thr Ser Leu Gly Ser Gly Pro Val Ser
        595                 600                 605

Val Ser Gly Val Gly Val Leu Ala Pro His Ala Ala Leu Ala Val Leu
    610                 615                 620

Glu Asp Thr Val Asp Tyr Pro Ala Arg Ala His Thr Phe Asp Asp Phe
625                 630                 635                 640

Cys Pro Glu Cys Arg Thr Leu Gly Leu Gln Gly Cys Ala Phe Gln Ser
                645                 650                 655

Thr Val Ala Glu Leu Gln Arg Leu Lys Met Arg Val Gly Lys Thr Arg
            660                 665                 670

Glu Phe

<210> SEQ ID NO 6
<211> LENGTH: 660
<212> TYPE: PRT
<213> ORGANISM: Hepatitis E virus

<400> SEQUENCE: 6

Met Arg Pro Arg Ala Val Leu Leu Leu Phe Leu Met Leu Leu Pro Met
1               5                   10                  15

Leu Pro Ala Pro Pro Ala Gly Gln Pro Ser Gly Arg Arg Arg Gly Arg
                20                  25                  30

Arg Ser Gly Gly Ser Gly Gly Gly Phe Trp Gly Asp Arg Val Asp Ser
            35                  40                  45

Gln Pro Phe Ala Leu Pro Tyr Ile His Pro Thr Asn Pro Phe Ala Ser
        50                  55                  60

Asp Val Ser Thr Ser Ala Gly Ala Gly Ala Arg Ala Arg Gln Ala Ala
65                  70                  75                  80

Arg Pro Leu Gly Ser Ala Trp Arg Asp Gln Ser Gln Arg Pro Ser Ala
                85                  90                  95

Ser Ala Arg Arg Arg Pro Thr Pro Ala Gly Ala Ser Pro Leu Thr Ala
            100                 105                 110

Val Ala Pro Ala Pro Asp Thr Thr Pro Val Pro Asp Val Asp Ser Arg
        115                 120                 125

Gly Ala Ile Leu Arg Arg Gln Tyr Asn Leu Ser Thr Ser Pro Leu Thr
130                 135                 140

Ser Thr Val Ala Ser Gly Thr Asn Leu Val Leu Tyr Ala Ala Pro Leu
145                 150                 155                 160

Gly Pro Leu Leu Pro Leu Gln Asp Gly Thr Asn Thr His Ile Met Ala
                165                 170                 175

Thr Glu Ala Ser Asn Tyr Ala Gln Tyr Arg Val Ile Arg Ala Thr Ile
            180                 185                 190

Arg Tyr Arg Pro Leu Val Pro Asn Ala Val Gly Gly Tyr Ala Ile Ser
        195                 200                 205
```

-continued

```
Ile Ser Phe Trp Pro Gln Thr Thr Thr Pro Thr Ser Val Asp Met
    210                 215                 220

Asn Ser Ile Thr Ser Thr Asp Val Arg Ile Leu Val Gln Pro Gly Leu
225                 230                 235                 240

Ala Ser Glu Leu Ile Ile Pro Ser Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Pro Asp
                325                 330                 335

Gly Thr Ala Glu Leu Thr Thr Thr Ala Ala Thr Arg Phe Met Lys Asp
            340                 345                 350

Leu Tyr Phe Thr Gly Ser Asn Gly Leu Gly Glu Val Gly Arg Gly Ile
    355                 360                 365

Ala Leu Thr Leu Phe Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Glu Ile Asp
            420                 425                 430

Leu Gly Asp Ser Arg Val Thr Ile Gln Asp Tyr Asp Asn Gln His Glu
    435                 440                 445

Gln Asp Arg Pro Thr Pro Ser Pro Ala Pro Ser Arg Pro Phe Ser Val
    450                 455                 460

Leu Arg Val Asn Asp Val Leu Trp Leu Thr Leu Thr Ala Ala Glu Tyr
465                 470                 475                 480

Asp Gln Thr Thr Tyr Gly Ser Thr Thr Asn Pro Met Tyr Val Ser Asp
                485                 490                 495

Thr Val Thr Phe Val Asn Val Ala Thr Gly Ala Gln Gly Val Ala Arg
            500                 505                 510

Ala Leu Asp Trp Ser Lys Val Thr Phe Asp Gly Arg Pro Leu Thr Thr
    515                 520                 525

Val Gln Gln Tyr Gly Lys Ser Phe Phe Val Leu Pro Leu Arg Gly Lys
    530                 535                 540

Leu Ser Phe Trp Glu Ala Gly Thr Val Lys Ala Gly Tyr Pro Tyr Asn
545                 550                 555                 560

Tyr Asn Thr Thr Ala Ser Asp Gln Ile Leu Val Glu Asn Ala Pro Gly
                565                 570                 575

His Arg Val Cys Ile Ser Thr Tyr Thr Thr Asn Leu Gly Ser Gly Pro
            580                 585                 590

Val Ser Ile Ser Ala Val Gly Val Leu Ala Pro His Ala Thr Ala
    595                 600                 605

Ala Leu Glu Asp Thr Ala Asp Ser Pro Ala Arg Ala His Thr Phe Asp
610                 615                 620

Asp Phe Cys Pro Glu Cys Arg Ile Leu Gly Leu Gln Gly Cys Ala Tyr
```

```
625                 630                 635                 640
    Gln Ser Thr Ala Ala Glu Leu Gln Arg Leu Lys Met Lys Val Gly Lys
                    645                 650                 655

Ser Arg Glu Phe
                660

<210> SEQ ID NO 7
<211> LENGTH: 497
<212> TYPE: PRT
<213> ORGANISM: Hepatitis E virus

<400> SEQUENCE: 7

Ala Val Ala Pro Ala His Asp Thr Pro Val Pro Asp Val Asp Ser
1               5                   10                  15

Arg Gly Ala Ile Leu Arg Arg Gln Tyr Asn Leu Ser Thr Ser Pro Leu
                20                  25                  30

Thr Ser Ser Val Ala Thr Gly Thr Asn Leu Val Leu Tyr Ala Ala Pro
                35                  40                  45

Leu Ser Pro Leu Leu Pro Leu Gln Asp Gly Thr Asn Thr His Ile Met
            50                  55                  60

Ala Thr Glu Ala Ser Asn Tyr Ala Gln Tyr Arg Val Val Arg Ala Thr
65                  70                  75                  80

Ile Arg Tyr Arg Pro Leu Val Pro Asn Ala Val Gly Gly Tyr Ala Ile
                85                  90                  95

Ser Ile Ser Phe Trp Pro Gln Thr Thr Thr Thr Pro Thr Ser Val Asp
                100                 105                 110

Met Asn Ser Ile Thr Ser Thr Asp Val Arg Ile Leu Val Gln Pro Gly
                115                 120                 125

Ile Ala Ser Glu His Val Ile Pro Ser Glu Arg Leu His Tyr Arg Asn
            130                 135                 140

Gln Gly Trp Arg Ser Val Glu Thr Ser Gly Val Ala Glu Glu Glu Ala
145                 150                 155                 160

Thr Ser Gly Leu Val Met Leu Cys Ile His Gly Ser Leu Val Asn Ser
                165                 170                 175

Tyr Thr Asn Thr Pro Tyr Thr Gly Ala Leu Gly Leu Leu Asp Phe Ala
                180                 185                 190

Leu Glu Leu Glu Phe Arg Asn Leu Thr Pro Gly Asn Thr Asn Thr Arg
            195                 200                 205

Val Ser Arg Tyr Ser Ser Thr Ala Arg His Arg Leu Arg Arg Gly Ala
            210                 215                 220

Asp Gly Thr Ala Glu Leu Thr Thr Thr Ala Ala Thr Arg Phe Met Lys
225                 230                 235                 240

Asp Leu Tyr Phe Thr Ser Thr Asn Gly Val Gly Glu Ile Gly Arg Gly
                245                 250                 255

Ile Ala Leu Thr Leu Phe Asn Leu Ala Asp Thr Leu Leu Gly Gly Leu
            260                 265                 270

Pro Thr Glu Leu Ile Ser Ser Ala Gly Gly Gln Leu Phe Tyr Ser Arg
            275                 280                 285

Pro Val Val Ser Ala Asn Gly Glu Pro Thr Val Lys Leu Tyr Thr Ser
            290                 295                 300

Val Glu Asn Ala Gln Gln Asp Lys Gly Ile Ala Ile Pro His Asp Ile
305                 310                 315                 320

Asp Leu Gly Glu Ser Arg Val Val Ile Gln Asp Tyr Asp Asn Gln His
                325                 330                 335
```

```
Glu Gln Asp Arg Pro Thr Pro Ser Pro Ala Pro Ser Arg Pro Phe Ser
            340                 345                 350

Val Leu Arg Ala Asn Asp Val Leu Trp Leu Ser Leu Thr Ala Ala Glu
            355                 360                 365

Tyr Asp Gln Ser Thr Tyr Gly Ser Ser Thr Gly Pro Val Tyr Val Ser
    370                 375                 380

Asp Ser Val Thr Leu Val Asn Val Ala Thr Gly Ala Gln Ala Val Ala
385                 390                 395                 400

Arg Ser Leu Asp Trp Thr Lys Val Thr Leu Asp Gly Arg Pro Leu Ser
                405                 410                 415

Thr Thr Gln Gln Tyr Ser Lys Thr Phe Phe Val Leu Pro Leu Arg Gly
            420                 425                 430

Lys Leu Ser Phe Trp Glu Ala Gly Thr Thr Lys Ala Gly Tyr Pro Tyr
            435                 440                 445

Asn Tyr Asn Thr Thr Ala Ser Asp Gln Leu Leu Val Glu Asn Ala Ala
            450                 455                 460

Gly His Arg Val Ala Ile Ser Thr Tyr Thr Thr Ser Leu Gly Ala Gly
465                 470                 475                 480

Pro Val Ser Ile Ser Ala Val Ala Val Leu Ala Pro His Ser Ala Leu
                485                 490                 495

Ala

<210> SEQ ID NO 8
<211> LENGTH: 497
<212> TYPE: PRT
<213> ORGANISM: Hepatitis E virus

<400> SEQUENCE: 8

Ala Ile Ser Pro Ala Pro Asp Thr Ala Pro Val Pro Asp Val Asp Ser
1               5                   10                  15

Arg Gly Ala Ile Leu Arg Arg Gln Tyr Asn Leu Ser Thr Ser Pro Leu
                20                  25                  30

Thr Ser Ser Val Ala Ser Gly Thr Asn Leu Val Leu Tyr Ala Ala Pro
            35                  40                  45

Leu Asn Pro Leu Leu Pro Leu Gln Asp Gly Thr Asn Thr His Ile Met
    50                  55                  60

Ala Thr Glu Ala Ser Asn Tyr Ala Gln Tyr Arg Val Val Arg Ala Thr
65                  70                  75                  80

Ile Arg Tyr Arg Pro Leu Val Pro Asn Ala Val Gly Gly Tyr Ala Ile
                85                  90                  95

Ser Ile Ser Phe Trp Pro Gln Thr Thr Thr Thr Pro Thr Ser Val Asp
            100                 105                 110

Met Asn Ser Ile Thr Ser Thr Asp Val Arg Ile Leu Val Gln Pro Gly
        115                 120                 125

Ile Ala Ser Glu Leu Val Ile Pro Ser Glu Arg Leu His Tyr Arg Asn
    130                 135                 140

Gln Gly Trp Arg Ser Val Glu Thr Thr Gly Val Ala Glu Glu Glu Ala
145                 150                 155                 160

Thr Ser Gly Leu Val Met Leu Cys Ile His Gly Ser Pro Val Asn Ser
                165                 170                 175

Tyr Thr Asn Thr Pro Tyr Thr Gly Ala Leu Gly Leu Leu Asp Phe Ala
            180                 185                 190

Leu Glu Leu Glu Phe Arg Asn Leu Thr Pro Gly Asn Thr Asn Thr Arg
        195                 200                 205
```

```
Val Ser Arg Tyr Thr Ser Thr Ala Arg His Arg Leu Arg Arg Gly Ala
    210                 215                 220

Asp Gly Thr Ala Glu Leu Thr Thr Thr Ala Ala Thr Arg Phe Met Lys
225                 230                 235                 240

Asp Leu His Phe Thr Gly Thr Asn Gly Val Gly Glu Val Gly Arg Gly
                245                 250                 255

Ile Ala Leu Thr Leu Phe Asn Leu Ala Asp Thr Leu Leu Gly Gly Leu
                260                 265                 270

Pro Thr Glu Leu Ile Ser Ser Ala Gly Gly Gln Leu Phe Tyr Ser Arg
            275                 280                 285

Pro Val Val Ser Ala Asn Gly Glu Pro Thr Val Lys Leu Tyr Thr Ser
290                 295                 300

Val Glu Asn Ala Gln Gln Asp Lys Gly Ile Thr Ile Pro His Asp Ile
305                 310                 315                 320

Asp Leu Gly Asp Ser Arg Val Val Ile Gln Asp Tyr Asp Asn Gln His
                325                 330                 335

Glu Gln Asp Arg Pro Thr Pro Ser Pro Ala Pro Ser Arg Pro Phe Ser
            340                 345                 350

Val Leu Arg Ala Asn Asp Val Leu Trp Leu Ser Leu Thr Ala Ala Glu
            355                 360                 365

Tyr Asp Gln Thr Thr Tyr Gly Ser Ser Thr Asn Pro Met Tyr Val Ser
            370                 375                 380

Asp Thr Val Thr Phe Val Asn Val Ala Thr Gly Ala Gln Ala Val Ala
385                 390                 395                 400

Arg Ser Leu Asp Trp Ser Lys Val Thr Leu Asp Gly Arg Pro Leu Thr
                405                 410                 415

Thr Ile Gln Gln Tyr Ser Lys Thr Phe Tyr Val Leu Pro Leu Arg Gly
            420                 425                 430

Lys Leu Ser Phe Trp Glu Ala Gly Thr Thr Lys Ala Gly Tyr Pro Tyr
            435                 440                 445

Asn Tyr Asn Thr Thr Ala Ser Asp Gln Ile Leu Ile Glu Asn Ala Ala
            450                 455                 460

Gly His Arg Val Ala Ile Ser Thr Tyr Thr Thr Ser Leu Gly Ala Gly
465                 470                 475                 480

Pro Thr Ser Ile Ser Ala Val Gly Val Leu Ala Pro His Ser Ala Leu
                485                 490                 495

Ala

<210> SEQ ID NO 9
<211> LENGTH: 497
<212> TYPE: PRT
<213> ORGANISM: Hepatitis E virus

<400> SEQUENCE: 9

Ala Val Ala Pro Ala Pro Asp Thr Ala Pro Val Pro Asp Val Asp Ser
1               5                   10                  15

Arg Gly Ala Ile Leu Arg Arg Gln Tyr Asn Leu Ser Thr Ser Pro Leu
                20                  25                  30

Thr Ser Thr Ile Ala Thr Gly Thr Asn Leu Val Leu Tyr Ala Ala Pro
            35                  40                  45

Leu Ser Pro Leu Leu Pro Leu Gln Asp Gly Thr Asn Thr His Ile Ile
        50                  55                  60

Ala Thr Glu Ala Ser Asn Tyr Ala Gln Tyr Arg Val Val Arg Ala Thr
65                  70                  75                  80
```

```
Ile Arg Tyr Arg Pro Leu Val Pro Asn Ala Val Gly Gly Tyr Ala Ile
                85                  90                  95

Ser Ile Ser Phe Trp Pro Gln Thr Thr Thr Pro Thr Ser Val Asp
            100                 105                 110

Met Asn Ser Ile Thr Ser Thr Asp Val Arg Ile Leu Val Gln Pro Gly
            115                 120                 125

Ile Ala Ser Glu Leu Val Ile Pro Ser Glu Arg Leu His Tyr Arg Asn
130                 135                 140

Gln Gly Trp Arg Ser Val Glu Thr Ser Gly Val Ala Glu Glu Ala
145                 150                 155                 160

Thr Ser Gly Leu Val Met Leu Cys Ile His Gly Ser Pro Val Asn Ser
                165                 170                 175

Tyr Thr Asn Thr Pro Tyr Thr Gly Ala Leu Gly Leu Leu Asp Phe Ala
                180                 185                 190

Leu Glu Leu Glu Phe Arg Asn Leu Thr Pro Gly Asn Thr Asn Thr Arg
                195                 200                 205

Val Ser Arg Tyr Ser Ser Ala Arg His Lys Leu Cys Arg Gly Pro
210                 215                 220

Asp Gly Thr Ala Glu Leu Thr Thr Thr Ala Ala Thr Arg Phe Met Lys
225                 230                 235                 240

Asp Leu His Phe Thr Gly Thr Asn Gly Val Gly Glu Val Gly Arg Gly
                245                 250                 255

Ile Ala Leu Thr Leu Leu Asn Leu Ala Asp Thr Leu Leu Gly Gly Leu
                260                 265                 270

Pro Thr Glu Leu Ile Ser Ser Ala Gly Gly Gln Leu Phe Tyr Ser Arg
                275                 280                 285

Pro Val Val Ser Ala Asn Gly Glu Pro Thr Val Lys Leu Tyr Thr Ser
290                 295                 300

Val Glu Asn Ala Gln Gln Asp Lys Gly Ile Ala Ile Pro His Asp Ile
305                 310                 315                 320

Asp Leu Gly Glu Ser Arg Val Val Ile Gln Asp Tyr Asp Asn Gln His
                325                 330                 335

Glu Gln Asp Arg Pro Thr Pro Ser Pro Ala Pro Ser Arg Pro Phe Ser
                340                 345                 350

Val Leu Arg Ala Asn Asp Val Leu Trp Leu Ser Leu Thr Ala Ala Glu
                355                 360                 365

Tyr Asp Gln Thr Thr Tyr Gly Ser Ser Thr Asn Pro Met Tyr Val Ser
                370                 375                 380

Asp Thr Val Thr Phe Val Asn Val Ala Thr Gly Thr Gln Gly Val Ser
385                 390                 395                 400

Arg Ser Leu Asp Trp Ser Lys Val Thr Leu Asp Gly Arg Pro Leu Thr
                405                 410                 415

Thr Ile Gln Gln Tyr Ser Lys Thr Phe Phe Val Leu Pro Leu Arg Gly
                420                 425                 430

Lys Leu Ser Phe Trp Glu Ala Gly Thr Thr Lys Ala Gly Tyr Pro Tyr
                435                 440                 445

Asn Tyr Asn Thr Thr Ala Ser Asp Gln Ile Leu Ile Glu Asn Ala Pro
450                 455                 460

Gly His Arg Val Cys Ile Ser Thr Tyr Thr Thr Asn Leu Gly Ser Gly
465                 470                 475                 480

Pro Val Ser Ile Ser Ala Val Gly Val Leu Ala Pro His Ser Ala Leu
                485                 490                 495

Ala
```

<210> SEQ ID NO 10
<211> LENGTH: 497
<212> TYPE: PRT
<213> ORGANISM: Hepatitis E virus

<400> SEQUENCE: 10

```
Ala Val Ala Pro Ala His Asp Thr Ser Pro Val Pro Asp Val Asp Ser
1               5                   10                  15

Arg Gly Ala Ile Leu Arg Arg Gln Tyr Asn Leu Ser Thr Ser Pro Leu
            20                  25                  30

Thr Ser Ser Val Ala Ser Gly Thr Asn Leu Val Leu Tyr Ala Ala Pro
        35                  40                  45

Leu Asn Pro Pro Leu Pro Leu Gln Asp Gly Thr Asn Thr His Ile Met
    50                  55                  60

Ala Thr Glu Ala Ser Asn Tyr Ala Gln Tyr Arg Val Ala Arg Ala Thr
65                  70                  75                  80

Ile Arg Tyr Arg Pro Leu Val Pro Asn Ala Val Gly Gly Tyr Ala Ile
                85                  90                  95

Ser Ile Ser Phe Trp Pro Gln Thr Thr Thr Thr Pro Thr Ser Val Asp
            100                 105                 110

Met Asn Ser Ile Thr Ser Thr Asp Val Arg Ile Leu Val Gln Pro Gly
        115                 120                 125

Ile Ala Ser Glu Leu Val Ile Pro Ser Glu Arg Leu His Tyr Arg Asn
    130                 135                 140

Gln Gly Trp Arg Ser Val Glu Thr Ser Gly Val Ala Glu Glu Glu Ala
145                 150                 155                 160

Thr Ser Gly Leu Val Met Leu Cys Ile His Gly Ser Pro Val Asn Ser
                165                 170                 175

Tyr Thr Asn Thr Pro Tyr Thr Gly Ala Leu Gly Leu Leu Asp Phe Ala
            180                 185                 190

Leu Glu Leu Glu Phe Arg Asn Leu Thr Thr Cys Asn Thr Asn Thr Arg
        195                 200                 205

Val Ser Arg Tyr Ser Ser Thr Ala Arg His Ser Ala Arg Gly Ala Asp
    210                 215                 220

Gly Thr Ala Glu Leu Thr Thr Ala Ala Thr Arg Phe Met Lys Asp
225                 230                 235                 240

Leu His Phe Thr Gly Leu Asn Gly Val Gly Glu Val Gly Arg Gly Ile
                245                 250                 255

Ala Leu Thr Leu Leu Asn Leu Ala Asp Thr Leu Leu Gly Gly Leu Pro
            260                 265                 270

Thr Glu Leu Ile Ser Ser Ala Gly Gly Gln Leu Phe Tyr Ser Arg Pro
        275                 280                 285

Val Val Ser Ala Asn Gly Glu Pro Thr Val Lys Leu Tyr Thr Ser Val
    290                 295                 300

Glu Asn Ala Gln Gln Asp Lys Gly Val Ala Ile Pro His Asp Ile Asp
305                 310                 315                 320

Leu Gly Asp Ser Arg Val Val Ile Gln Asp Tyr Asp Asn Gln His Glu
                325                 330                 335

Gln Asp Arg Pro Thr Pro Ser Pro Ala Pro Ser Arg Pro Phe Ser Val
            340                 345                 350

Leu Arg Ala Asn Asp Val Leu Trp Leu Ser Leu Thr Ala Ala Glu Tyr
        355                 360                 365

Asp Gln Ser Thr Tyr Gly Ser Ser Thr Gly Pro Val Tyr Ile Ser Asp
```

```
                     370                 375                 380
Ser Val Thr Leu Val Asn Val Ala Thr Gly Ala Gln Ala Val Ala Arg
385                 390                 395                 400

Ser Leu Asp Trp Ser Lys Val Thr Leu Asp Gly Arg Pro Leu Pro Thr
                405                 410                 415

Val Glu Gln Tyr Ser Lys Thr Phe Phe Val Leu Pro Leu Arg Gly Lys
                420                 425                 430

Leu Ser Phe Trp Glu Ala Gly Thr Thr Lys Ala Gly Tyr Pro Tyr Asn
                435                 440                 445

Tyr Asn Thr Thr Ala Ser Asp Gln Ile Leu Ile Glu Asn Ala Ala Gly
                450                 455                 460

His Arg Val Ala Ile Ser Thr Tyr Thr Thr Arg Leu Gly Ala Gly Pro
465                 470                 475                 480

Val Ala Ile Ser Ala Ala Ala Val Leu Ala Pro Arg Ser Ala Leu Ala
                485                 490                 495

Leu

<210> SEQ ID NO 11
<211> LENGTH: 497
<212> TYPE: PRT
<213> ORGANISM: Hepatitis E virus
<220> FEATURE:
<221> NAME/KEY: MOD_RES
<222> LOCATION: (257)..(257)
<223> OTHER INFORMATION: Any amino acid

<400> SEQUENCE: 11

Ser Arg Arg Arg Ser Thr Pro Thr Gly Ala Ser Pro Leu Thr Ala Val
1               5                   10                  15

Ala Pro Ala Pro Asp Thr Arg Pro Val Pro Asp Val Asp Ser Arg Gly
                20                  25                  30

Ala Ile Leu Arg Arg Gln Tyr Asn Leu Ser Thr Ser Pro Leu Thr Ser
                35                  40                  45

Thr Ile Ala Ser Gly Thr Asn Leu Val Leu Tyr Ala Ala Pro Leu Ser
    50                  55                  60

Pro Leu Leu Pro Leu Gln Asp Gly Thr Asn Thr His Ile Met Ala Thr
65                  70                  75                  80

Glu Ala Ser Asn Tyr Ala Gln Tyr Arg Val Val Arg Ala Thr Ile Arg
                85                  90                  95

Tyr Arg Pro Leu Val Pro Asn Ala Val Gly Gly Tyr Ala Ile Ser Ile
                100                 105                 110

Ser Phe Trp Pro Gln Thr Thr Thr Thr Pro Thr Ser Val Asp Met Asn
                115                 120                 125

Ser Ile Thr Ser Thr Asp Val Arg Ile Val Val Gln Pro Gly Leu Ala
    130                 135                 140

Ser Glu Leu Val Ile Pro Ser Glu Arg Leu His Tyr Arg Asn Gln Gly
145                 150                 155                 160

Trp Arg Ser Val Glu Thr Ser Gly Val Ala Glu Glu Ala Thr Ser
                165                 170                 175

Gly Leu Val Met Leu Cys Ile His Gly Ser Pro Val Asn Ser Tyr Thr
                180                 185                 190

Asn Thr Pro Tyr Thr Gly Ala Leu Gly Leu Leu Asp Phe Ala Leu Glu
                195                 200                 205

Leu Glu Phe Arg Asn Leu Thr Pro Gly Asn Thr Asn Thr Arg Val Ser
    210                 215                 220
```

```
Arg Tyr Ser Ser Thr Ala Arg His Arg Leu His Arg Gly Ala Asp Gly
225                 230                 235                 240

Thr Ala Glu Leu Thr Thr Thr Ala Ala Thr Arg Phe Met Lys Asp Leu
            245                 250                 255

Xaa Phe Thr Gly Ser Asn Gly Ile Gly Glu Val Gly Arg Gly Ile Ala
        260                 265                 270

Leu Thr Leu Phe Asn Leu Ala Asp Thr Leu Leu Gly Gly Leu Pro Thr
        275                 280                 285

Glu Leu Ile Ser Ser Ala Gly Gly Gln Leu Phe Tyr Ser Arg Pro Val
290                 295                 300

Val Ser Ala Asn Gly Glu Pro Thr Val Lys Leu Tyr Thr Ser Val Glu
305                 310                 315                 320

Asn Ala Gln Gln Asp Lys Gly Ile Ala Ile Pro His Asp Ile Asp Leu
                325                 330                 335

Gly Asp Ser Arg Val Val Ile Gln Asp Tyr Asp Asn Gln His Glu Gln
            340                 345                 350

Asp Arg Pro Thr Pro Ser Pro Ala Pro Ser Arg Pro Phe Ser Val Leu
        355                 360                 365

Arg Val Asn Asp Val Leu Trp Leu Thr Met Thr Ala Ala Glu Tyr Asp
370                 375                 380

Gln Thr Thr Tyr Gly Thr Ser Thr Asp Pro Val Tyr Val Ser Asp Thr
385                 390                 395                 400

Val Thr Phe Val Asn Val Ala Thr Gly Ala Gln Gly Val Ala Arg Ser
                405                 410                 415

Leu Asp Trp Ser Lys Val Thr Leu Asp Gly Arg Pro Leu Thr Thr Ile
            420                 425                 430

Gln Arg His Ser Lys Asn Tyr Phe Val Leu Pro Leu Arg Gly Lys Leu
        435                 440                 445

Ser Phe Trp Glu Ala Gly Thr Thr Lys Ala Gly Tyr Pro Tyr Asn Tyr
    450                 455                 460

Asn Thr Thr Ala Ser Asp Gln Ile Leu Ile Glu Asn Ala Ala Gly His
465                 470                 475                 480

Arg Val Cys Ile Ser Thr Tyr Thr Thr Ser Leu Gly Ser Gly Pro Val
                485                 490                 495

Ser
```

<210> SEQ ID NO 12
<211> LENGTH: 497
<212> TYPE: PRT
<213> ORGANISM: Hepatitis E virus

<400> SEQUENCE: 12

```
Ala Val Ala Pro Ala Pro Asp Thr Thr Pro Val Pro Asp Val Asp Ser
1               5                   10                  15

Arg Gly Ala Ile Leu Arg Arg Gln Tyr Asn Leu Ser Thr Ser Pro Leu
            20                  25                  30

Thr Ser Thr Val Ala Ser Gly Thr Asn Leu Val Leu Tyr Ala Ala Pro
        35                  40                  45

Leu Gly Pro Leu Leu Pro Leu Gln Asp Gly Thr Asn Thr His Ile Met
    50                  55                  60

Ala Thr Glu Ala Ser Asn Tyr Ala Gln Tyr Arg Val Ile Arg Ala Thr
65                  70                  75                  80

Ile Arg Tyr Arg Pro Leu Val Pro Asn Ala Val Gly Gly Tyr Ala Ile
                85                  90                  95
```

```
Ser Ile Ser Phe Trp Pro Gln Thr Thr Thr Pro Thr Ser Val Asp
            100                 105                 110

Met Asn Ser Ile Thr Ser Asp Val Arg Ile Leu Val Gln Pro Gly
        115                 120                 125

Leu Ala Ser Glu Leu Ile Ile Pro Ser Glu Arg Leu His Tyr Arg Asn
130                 135                 140

Gln Gly Trp Arg Ser Val Glu Thr Ser Gly Val Ala Glu Glu Ala
145                 150                 155                 160

Thr Ser Gly Leu Val Met Leu Cys Ile His Gly Ser Pro Val Asn Ser
                165                 170                 175

Tyr Thr Asn Thr Pro Tyr Thr Gly Ala Leu Gly Leu Leu Asp Phe Ala
            180                 185                 190

Leu Glu Leu Glu Phe Arg Asn Leu Thr Pro Gly Asn Thr Asn Thr Arg
        195                 200                 205

Val Ser Arg Tyr Thr Ser Thr Ala Arg His Arg Leu Arg Arg Gly Pro
    210                 215                 220

Asp Gly Thr Ala Glu Leu Thr Thr Ala Ala Thr Arg Phe Met Lys
225                 230                 235                 240

Asp Leu Tyr Phe Thr Gly Ser Asn Gly Leu Gly Glu Val Gly Arg Gly
                245                 250                 255

Ile Ala Leu Thr Leu Phe Asn Leu Ala Asp Thr Leu Leu Gly Gly Leu
            260                 265                 270

Pro Thr Glu Leu Ile Ser Ser Ala Gly Gln Leu Phe Tyr Ser Arg
        275                 280                 285

Pro Val Val Ser Ala Asn Gly Glu Pro Thr Val Lys Leu Tyr Thr Ser
    290                 295                 300

Val Glu Asn Ala Gln Gln Asp Lys Gly Ile Ala Ile Pro His Glu Ile
305                 310                 315                 320

Asp Leu Gly Asp Ser Arg Val Thr Ile Gln Asp Tyr Asp Asn Gln His
                325                 330                 335

Glu Gln Asp Arg Pro Thr Pro Ser Pro Ala Pro Ser Arg Pro Phe Ser
            340                 345                 350

Val Leu Arg Val Asn Asp Val Leu Trp Leu Thr Leu Thr Ala Ala Glu
        355                 360                 365

Tyr Asp Gln Thr Thr Tyr Gly Ser Thr Thr Asn Pro Met Tyr Val Ser
370                 375                 380

Asp Thr Val Thr Phe Val Asn Val Ala Thr Gly Ala Gln Gly Val Ala
385                 390                 395                 400

Arg Ala Leu Asp Trp Ser Lys Val Thr Phe Asp Gly Arg Pro Leu Thr
                405                 410                 415

Thr Val Gln Gln Tyr Gly Lys Ser Phe Phe Val Leu Pro Leu Arg Gly
            420                 425                 430

Lys Leu Ser Phe Trp Glu Ala Gly Thr Val Lys Ala Gly Tyr Pro Tyr
        435                 440                 445

Asn Tyr Asn Thr Thr Ala Ser Asp Gln Ile Leu Val Glu Asn Ala Pro
    450                 455                 460

Gly His Arg Val Cys Ile Ser Thr Tyr Thr Thr Asn Leu Gly Ser Gly
465                 470                 475                 480

Pro Val Ser Ile Ser Ala Val Gly Val Leu Ala Pro His Ala Ala Thr
                485                 490                 495

Ala

<210> SEQ ID NO 13
```

-continued

```
<211> LENGTH: 6
<212> TYPE: PRT
<213> ORGANISM: Hepatitis E virus

<400> SEQUENCE: 13

Leu Asp Gly Arg Pro Leu
1               5

<210> SEQ ID NO 14
<211> LENGTH: 7
<212> TYPE: PRT
<213> ORGANISM: Hepatitis E virus

<400> SEQUENCE: 14

Val Ser Ala Asn Gly Glu Pro
1               5

<210> SEQ ID NO 15
<211> LENGTH: 7
<212> TYPE: PRT
<213> ORGANISM: Hepatitis E virus

<400> SEQUENCE: 15

Thr Leu Asp Gly Arg Pro Leu
1               5
```